US008034783B2

(12) United States Patent
Moss et al.

(10) Patent No.: US 8,034,783 B2
(45) Date of Patent: *Oct. 11, 2011

(54) PRODOMAIN MODULATORS OF ADAM 10

(75) Inventors: Marcia Moss, Apex, NC (US); Pei Zhou, Durham, NC (US)

(73) Assignees: Biozyme, Inc., Apex, NC (US); Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/580,682

(22) Filed: Oct. 16, 2009

(65) Prior Publication Data

US 2010/0081620 A1    Apr. 1, 2010

Related U.S. Application Data

(62) Division of application No. 11/897,018, filed on Aug. 28, 2007, now Pat. No. 7,638,301.

(60) Provisional application No. 60/823,714, filed on Aug. 28, 2006.

(51) Int. Cl.
*A61K 38/16* (2006.01)
*C07K 1/00* (2006.01)
*C07K 14/00* (2006.01)

(52) U.S. Cl. .................. 514/21.2; 530/350; 530/402

(58) Field of Classification Search .................. None
See application file for complete search history.

(56) References Cited

U.S. PATENT DOCUMENTS

| | | | |
|---|---|---|---|
| 4,554,101 A | 11/1985 | Hopp | |
| 5,922,546 A | 7/1999 | Mayer et al. | |
| 5,935,792 A | 8/1999 | Rubin et al. | |
| 6,319,681 B1 | 11/2001 | Dalie et al. | |
| 6,319,704 B1 | 11/2001 | Rubin et al. | |
| 6,399,350 B1 | 6/2002 | Rubin et al. | |
| 6,531,290 B2 | 3/2003 | Dalie et al. | |
| 7,638,301 B2 | 12/2009 | Moss et al. | |
| 2008/0096820 A1 | 4/2008 | Moss et al. | |

OTHER PUBLICATIONS

Fahrenholz et al 2000. Ann NY Acad Sci 920:215-222.*
Moss et al. 2007. J. Biol. Chem. 282:35712-35721.*
Anders et al., "Regulation of the α-Secretase ADAM10 by Its Prodomain and Proprotein Convertases," The FASEB Journal, Published online (Jun. 27, 2001).
Black et al., "Substrate Specificity and Inducibility of TACE (Tumor Necrosis Factor α-Converting Enzyme) Revisited: the Ala-Val Preference, and Induced Intrinsic Activity," Biochem. Soc. Symp., vol. 70, pp. 39-52 (2003).
Blobel, "ADAMS: Key Components in EGFR Signalling and Development," Nature Reviews, Molecular Cell Biology, vol. 6, pp. 32-43 (Jan. 2005).
Budagian et al., "Soluble Axl Is Generated by ADAM10-Dependent Cleavage and Associates with Gas6 in Mouse Serum," Molecular and Cellular Biology, vol. 25, No. 21, pp. 9324-9339 (Nov. 2005).

Gonzales et al., "Inhibition of the Tumor Necrosis Factor-α-converting Enzyme by Its Pro Domain," The Journal of Biological Chemistry, vol. 279, No. 30, pp. 31638-31645 (Jul. 23, 2004).
Hart et al., "GPCR-induced migration of breast carcinoma cells depends on both EGFR signal transactivation and EGFR-independent pathways," Biol. Chem., vol. 386, pp. 845-855 (Sep. 2005).
Janes et al., "Adam Meets Eph: An ADAM Substrate Recognition Module Acts as a Molecular Switch for Ephrin Cleavage in Trans," Cell, vol. 123, pp. 291-304 (Oct. 21, 2005).
Kassouf et al., "Schedule Dependent Efficacy of Gefitinib and Docetaxel for Bladder Cancer," The Journal of Urology, vol. 176, pp. 787-792 (Aug. 2006).
Kilmon et al., "Metalloprotease inhibitor-mediated inhibition of mouse immunoglobulin production," Immunology, vol. 102, pp. 281-288 (2001).
Kyte et al., "A Simple Method for Displaying the Hydropathic Character of a Protein," J. Mol. Biol., vol. 157, pp. 105-132 (1982).
Lammich et al., "Constitutive and regulated α-secretase cleavage of Alzheimer's amyloid precursor protein by a disintegrin metalloprotease," Proc. Natl. Acad. Sci. USA, vol. 96, pp. 3922-3927 (Mar. 1999).
Lemieux et al., "The Low Affinity IgE Receptor (CD23) Is Cleaved by the Metalloproteinase ADAM10," The Journal of Biological Chemistry, vol. 282, No. 20, pp. 14836-14844 (May 18, 2007).
Ludwig et al., "Metalloproteinase Inhibitors for the Disintegrin-Like Metalloproteinases ADAM10 and ADAM17 that Differentially Block Constitutive and Phorbol Ester-Inducible Shedding of Cell Surface Molecules," Combinatorial Chemistry & High Throughput Screening, vol. 8, pp. 161-171 (2005).
Maretzky et al., "ADAM10 mediates E-cadherin shedding and regulates epithelial cell-cell adhesion, migration, and β-catenin translocation," PNAS, vol. 102, No. 26, pp. 9182-9187 (Jun. 28, 2005).
Milla et al., "Specific Sequence Elements Are Required for the Expression of Functional Tumor Necrosis Factor-α-converting Enzyme (TACE)," The Journal of Biological Chemistry, vol. 274, No. 43, pp. 30563-30570 (Oct. 22, 1999).
Moss et al., "Therapeutic Benefits from Targeting of ADAM Family Members," Biochemistry, vol. 43, No. 23 (Jun. 15, 2004). Naus et al., "Identification of Candidate Substrates for Ectodomain Shedding by the Metalloprotease-Disintegrin ADAM8," Biol. Chem., vol. 387, pp. 337-346 (Mar. 2006).
Pan et al., "Kuzbanian Controls Proteolytic Processing of Notch and Mediates Lateral Inhibition during *Drosophila* and Vertebrate Neurogenesis," Cell, vol. 90, pp. 271-280 (Jul. 25, 1997).
Postina et al., "A Disintegrin-Metalloproteinase Prevents Amyloid Plaque Formation and Hippocampal Defects in an Alzheimer Disease Mouse Model," J. Clin. Invest., vol. 113, pp. 1456-1464 (2004).
Reiss et al., "ADAM10 Cleavage of N-cadherin and Regulation of Cell-Cell Adhesion and β-Catenin Nuclear Signalling," The EMBO Journal, vol. 24, pp. 742-752 (2005).

(Continued)

*Primary Examiner* — Shulamith H Shafer
(74) *Attorney, Agent, or Firm* — Jenkins, Wilson, Taylor & Hunt, P.A.

(57) ABSTRACT

The presently disclosed subject matter discloses isolated ADAM 10 modulating peptides and related compounds useful for studying the biological functions of ADAM 10 and for the treatment of diseases such as cancer, neurological disorders, asthma, and allergic responses, and disorders characterized at least in part by the presence of one or more of inflammation, excess cell proliferation, angiogenesis, and excess soluble CD23. In one aspect, the presently disclosed subject matter provides isolated mouse and human ADAM 10 prodomain comprising the sequence set forth in SEQ ID NOs 1-8, or a sequence having at least 95% homology to any of SEQ ID NOs 1-8 and having the functionality of modulating ADAM 10 activity.

5 Claims, 3 Drawing Sheets

OTHER PUBLICATIONS

Rosenwasser et al., "Anti-CD23," Clinical Reviews in Allergy & Immunology, vol. 29, pp. 61-72 (2005).

Sahin et al., "Distinct roles for ADAM10 and ADAM17 in Ectodomain Shedding of Six EGFR Ligands," Journal of Cell Biology, vol. 164, No. 5, pp. 769-779 (Mar. 1, 2004).

Sanderson et al., "ADAM10 Mediates Ectodomain Shedding of the Betacellulin Precursor Activated by p-Aminophenylmercuric Acetate and Extracellular Calcium Influx," The Journal of Biological Chemistry, vol. 280, No. 3, pp. 1826-1837 (Jan. 21, 2005).

Wolfsberg et al., "ADAM, a Novel Family of Membrane Proteins Containing A Disintegrin And Metalloprotease Domain: Multipotential Functions in Cell-Cell and Cell-Matrix Interactions," The Journal of Cell Biology, vol. 131, No. 2, pp. 275-278 (Oct. 1995).

Wolfsberg et al., "Rapid Communication: ADAM, a Widely Distributed and Developmentally Regulated Gene Family Encoding Membrane Proteins with A Disintegrin And Metalloprotease Domain," Developmental Biology, vol. 169, pp. 378-383 (1995).

Bowie et al., "Deciphering the Message in Protein Sequences: Tolerance to Amino Acid Substitutions," Science, vol. 247, pp. 1306-1310 (1990).

Edwards et al., "The ADAM metalloproteinases," Molecular Aspects of Med., vol. 29, pp. 258-289 (2008).

Fahrenholz et al., "α-Secretase Activity of the Disintegrin Metalloprotease ADAM 10," Ann. NY Acad. Sci., vol. 920, pp. 215-222 (2000).

Gerhard et al., "The Status, Quality, and Expansion of the NIH Full-Length cDNA Project: The Mammalian Gene Collection (MGC)," Genome Res., vol. 14, pp. 2121-2127 (2004).

Liu et al., "Identification of ADAM10 as a Major Source of HER2 Ectodomain Sheddase Activity in HER2 Overexpressing Breast Cancer Cells," Cancer Biol. Ther., vol. 200, No. 5(6), pp. 657-664, 2006.

Ngo et al., "The Protein Folding Problem and Tertiary Structure Prediction," Merz et al. (eds.), Birkhauser, Boston, pp. 433-506 (1994).

Notice of Allowance corresponding to U.S. Appl. No. 11/897,018 dated Sep. 17, 2009.

Office Action corresponding to U.S. Appl. No. 11/897,018 dated Feb. 20, 2009.

Uniprot KB/Swiss-Prot 035598, downloaded Feb. 10, 2009.

Wells, "Additivity of Mutational Effects in Proteins," Biochemistry, vol. 29, pp. 8509-8517 (1990).

* cited by examiner

US 8,034,783 B2

PRODOMAIN MODULATORS OF ADAM 10

CROSS REFERENCE TO RELATED APPLICATIONS

This application is a divisional of U.S. patent application Ser. No. 11/897,018, filed Aug. 28, 2007 (now U.S. Pat. No. 7,638,301), which itself claims the benefit of U.S. Provisional Patent Application Ser. No. 60/823,714, filed Aug. 28, 2006. The disclosure of each of these applications is incorporated herein by reference in its entirety.

BACKGROUND

1. Field of the Presently Disclosed Subject Matter

The presently disclosed subject matter relates to compositions and methods pertaining to the modulation of ADAM 10. In particular, the presently disclosed subject matter relates to isolated and purified prodomain of ADAM 10, to truncations and mutations of prodomain polypeptides, and to modifications to stabilize prodomains for in vivo use. The presently disclosed subject matter further relates to the use of prodomains in cellular assays, and to the use of prodomains for treatment of diseases such as cancer, neurological disorders, asthma, and allergic responses.

2. Description of the Related Art

ADAM 10 is a member of the a disintegrin and metalloproteinase (ADAM) family (1) that includes enzymes such as TACE (ADAM 17), ADAM 8, and ADAM 9. In total, for humans, there are 33 ADAM family members. The ADAM proteins comprise a prodomain that is important for proper folding and transport of the enzyme through the cell, a catalytic domain containing a typical HEXXH motif, a disintegrin domain, that is used to interact with integrins, a cysteine rich region that is believed to be important for substrate recognition, a transmembrane domain, and a cytoplasmic tail that is involved in signaling events.

Members of the ADAM family are known to cleave type I and type II single membrane spanning proteins from cells to generate soluble mature proteins that have varying physiological roles (2). For example, TACE is known to generate soluble epidermal growth factor (EGF) ligands such as TGF-alpha, amphiregulin, and HBEGF (3). Similarly, ADAM 10 activity generates soluble proteins including, but not limited to, EGF ligands, EGF and betacellulin (3), Notch (4), amyloid precursor protein (5), ephrins (6), cadherins (7), protocadherins (8), chemokines such as CXCL16 and CX3CL1 (9), HER2 (10), AXL (11), and CD23, a low affinity receptor for IgE (12). Disruption of ADAM 10 activity has been shown to decrease the level of soluble non-amyloidogenic APP both in vivo and in cell based assays (13), suggesting that maintaining ADAM 10 activity may play a protective role in Alzheimers disease for normal processing of soluble APP-α. In contrast, excess ADAM 10 activity may promote cell growth in cancer proliferation assays due to enhanced production of soluble epidermal growth factor (EGF) ligands (14).

Inhibition of TACE activity is correlated with beneficial effects in a tumor cell proliferation assay (15). The mechanism for this inhibition of tumor cell proliferation is believed to be through prevention of EGF ligand release. For example, EGF ligands such as TGF-alpha, amphiregulin, HB-EGF, EGF and betacellulin, once released, are capable of activating the EGF receptor, which in turn leads to cancer proliferation (3). Similar to TACE, ADAM 10 promotes production of soluble EGF ligands such as EGF and betacellulin, however, unlike TACE, ADAM 10 also generates soluble Notch (4) and AXL (11) that are known promoters of tumor cell proliferation.

In addition to EGF ligands, ADAM 10 also generates soluble CD23 (12). Release of CD23 promotes allergic responses through activation of IgE (16). Metalloproteinase inhibitors have been shown to block CD23 shedding and prevent allergic responses in both in vitro and in vivo assays (17).

Accordingly, the ability to specifically modulate ADAM 10 activity would be useful to study the biological functions of the protein, and for the treatment of disorders including cancer, neurological disorders, asthma, and allergic responses. Unfortunately, existing small molecule inhibitors are not specific for ADAM 10 activity. For example, hydroxamates developed by GSK inhibit both ADAM 10, as well as other members of the matrix metalloproteinase family (9). Inhibitors disclosed by Incyte also inhibit MMPs, and possibly other ADAM family members (10). Such non-specific inhibition often leads to unwanted side effects, and in this case has prevented the compounds from being developed into pharmaceutical drugs (18).

Another approach to this problem is to use ADAM protein prodomains as selective inhibitors. ADAM family members are expressed as zymogens with the prodomains maintaining the enzymes in a latent state. However, while isolated prodomains have been shown to inhibit the proteolytic activity of ADAM family proteins in vitro, not all prodomains are good inhibitors. For example, the prodomain of TACE suppresses the activity of its catalytic domain with a $K_i$ of 50 nM (19), but the prodomain is only a weak (high micromolar) inhibitor of a TACE construct consisting of both the catalytic and disintegrin domains. Therefore, the prodomain is unlikely to negatively affect TACE activity in vivo, as the catalytic and disintegrin domains are both retained in membrane bound TACE.

Furthermore, for those prodomains that do inhibit ADAM activity, they have never been tested to determine if they are specific inhibitors of their respective ADAMs.

Accordingly, there is a need in the art for selective modulators of ADAM proteases to study the biological functions of the proteins and to treat diseases such as cancer, neurological disorders, asthma, and allergic responses.

SUMMARY

The presently disclosed subject matter discloses an isolated ADAM 10 modulating peptide and related compounds useful for studying the biological functions of ADAM 10 and for the treatment of diseases such as cancer, neurological disorders, asthma, and allergic responses, and disorders characterized at least in part by the presence of one or more of inflammation, excess cell proliferation, angiogenesis, and excess soluble CD23. Accordingly, the presently disclosed subject matter meets a long-standing need in the art for specific modulators of ADAM 10 activity.

In one aspect, the presently disclosed subject matter provides isolated mouse ADAM 10 prodomain comprising the sequence set forth in SEQ ID NOs 1-4, or a sequence having at least 95% homology to any of SEQ ID NOs 1-4 and having the functionality of modulating ADAM 10 activity. In another aspect, the presently disclosed subject matter provides isolated human ADAM 10 prodomain comprising the sequence set forth in SEQ ID NOs 5-8, or a sequence having at least 95% homology to any of SEQ ID NOs 5-8 and having the functionality of modulating ADAM 10 activity. In one aspect, the presently disclosed subject matter provides isolated mouse ADAM 10 prodomain consisting of the sequence set forth in SEQ ID NOs 1-4, or a sequence having at least 95% homology to any of SEQ ID NOs 1-4 and having the functionality of modulating ADAM 10 activity. In another aspect, the presently disclosed subject matter provides isolated human ADAM 10 prodomain consisting of the sequence set forth in SEQ ID NOs 5-8, or a sequence having at least 95% homology to any of SEQ ID NOs 5-8 and having the functionality of modulating ADAM 10 activity.

In another aspect, the presently disclosed subject matter provides isolated mouse ADAM 10 prodomain comprising an amino acid sequence present in amino acid residues 18-213 of mouse ADAM 10 protein, the peptide having the functionality of modulating ADAM 10 protein activity. In another aspect, the presently disclosed subject matter provides isolated human ADAM 10 prodomain comprising an amino acid sequence present in amino acid residues 18-212 of human ADAM 10 protein, the peptide having the functionality of modulating ADAM 10 protein activity. In another aspect, the presently disclosed subject matter provides isolated mouse ADAM 10 prodomain consisting of an amino acid sequence present in amino acid residues 18-213 of mouse ADAM 10 protein, the peptide having the functionality of modulating ADAM 10 protein activity. In another aspect, the presently disclosed subject matter provides isolated human ADAM 10 prodomain consisting of an amino acid sequence present in amino acid residues 18-212 of human ADAM 10 protein, the peptide having the functionality of modulating ADAM 10 protein activity. The ADAM 10 modulating peptides of the presently disclosed subject matter include modifications of the peptides such as the presence of non-natural amino acids, D- or D,L-racemic mixture isomer form, carboxy- or amino-terminus modifications such as tags, conjugation to biocompatible molecules including fatty acids and PEG, and amino acid chemical substitution.

In another aspect, the presently disclosed subject matter provides for polynucleotides that encode the ADAM 10 modulating peptides of the invention. The presently disclosed subject matter also provides expression vectors comprising the polynucleotides encoding the ADAM 10 modulating peptides of the invention. The presently disclosed subject matter further provides host cells comprising the expression vectors of the invention. In a further aspect of the present invention, a method is provided for preparing an ADAM 10 modulating peptide comprising transfecting a cell with a polynucleotide that encodes the ADAM 10 modulating peptide to produce a transformed host cell, and maintaining the transformed host cell under biological conditions sufficient for expression of the peptide.

Another aspect of the presently disclosed subject matter provides methods and compositions for modulating ADAM 10 activity in vitro and in vivo. In one aspect, the presently disclosed subject matter provides a method for modulating ADAM 10 activity in vitro: comprising contacting an ADAM 10 modulating prodomain with a solution or a cell comprising ADAM 10 protein, wherein the amount of the contacted prodomain is sufficient to modulate the activity of the ADAM 10 protein. In another aspect, the presently disclosed subject matter provides a method for decreasing the generation of one or more of soluble CD23, inflammation, or excess cell proliferation, comprising administering to an animal a composition or pharmaceutical formulation comprising an ADAM 10 modulating prodomain, to treat a disorder characterized at least in part by one or more of inflammation, allergic response, asthma, angiogenesis, cancer or a predisposition to such disorder.

An object of the presently disclosed subject matter having been stated above, other objects and advantages will become apparent upon a review of the following descriptions, figures, and examples.

DETAILED DESCRIPTION

Figure 1:
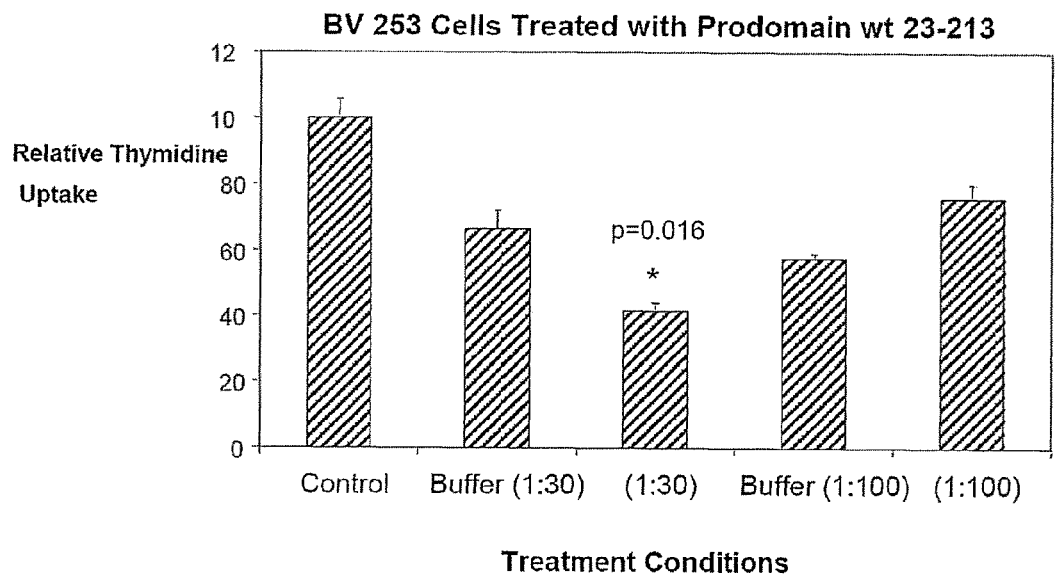
FIG. 1 is a set of bar graphs showing ADAM 10 prodomain inhibition of tumor cell proliferation in two bladder cancer cells lines, BV 253 and KU-7.
Figure 1:
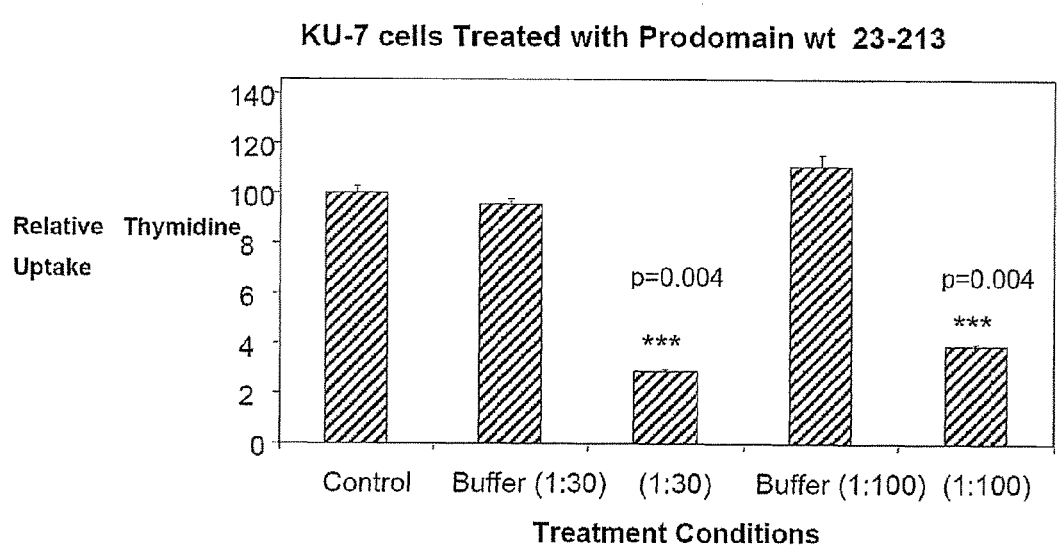
Figure 2:
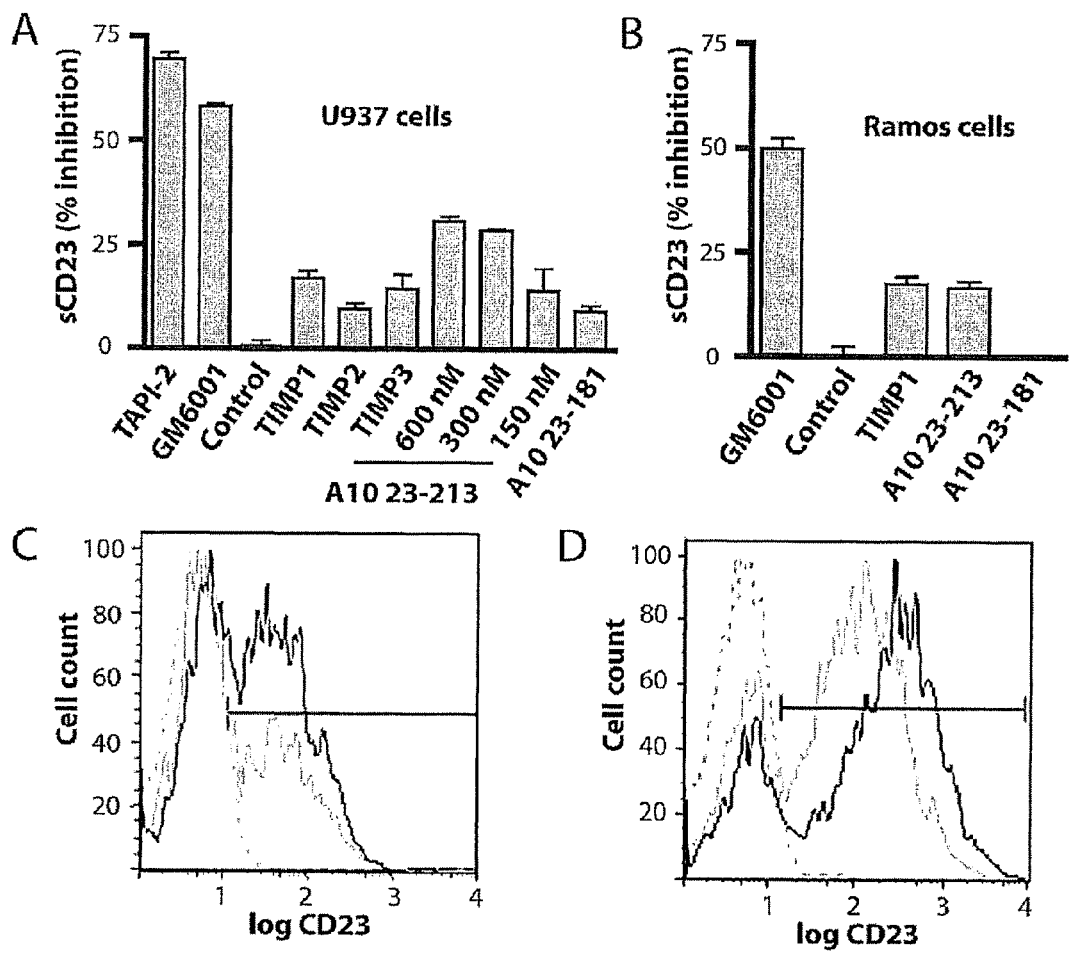
FIGS. 2A-2D show ADAM 10 prodomain inhibition of ADAM 10 sheddase activity in various cell lines. ADAM 10 prodomain (C to S mutant) inhibited about 30% of CD23 shedding in Ramos (FIG. 2A) and U937 cells (FIG. 2B). ADAM 10 prodomain (wild type) inhibition of shedding in B cells (FIG. 2C) and in B cells stimulated with IL-4 (FIG. 2D).
Figure 3:
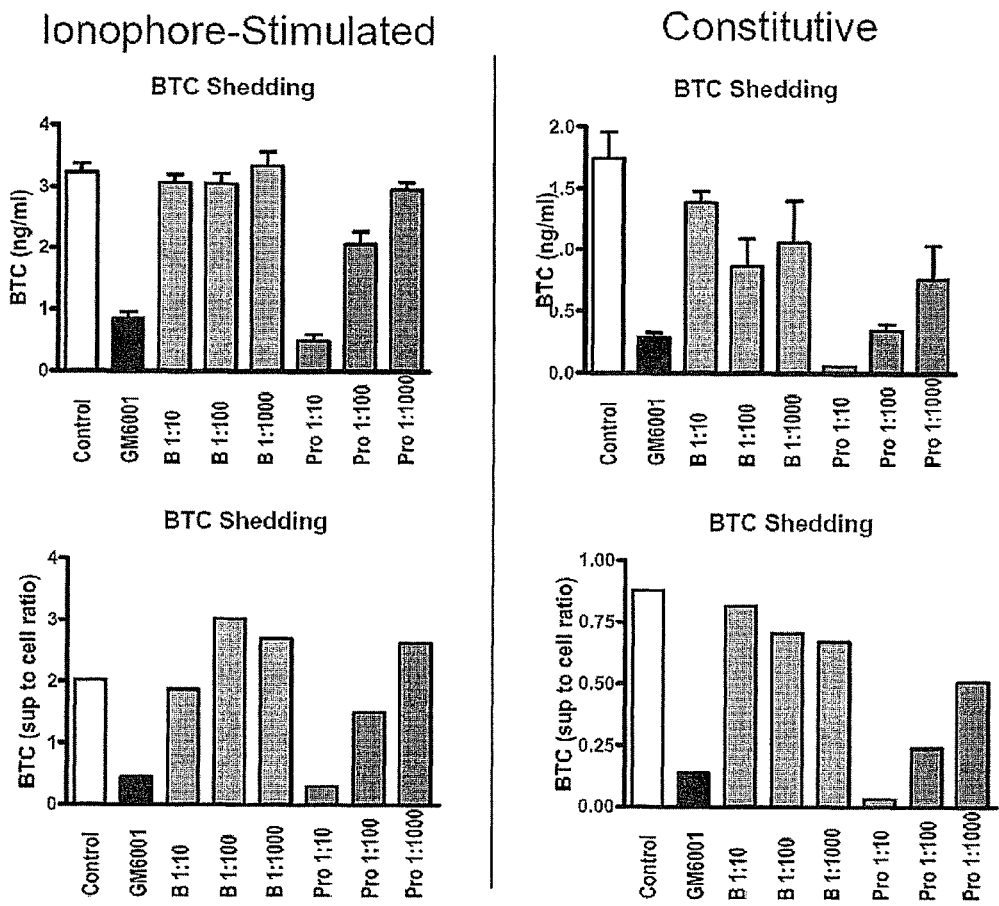
FIG. 3 is a set of bar graphs showing ADAM 10 prodomain inhibition of constitutive and calcium ionophore induced betacellulin shedding.

The presently disclosed subject matter provides prodomains of ADAM 10 that are able to inhibit, specifically, ADAM 10 protein activity both in the context of an enzyme assay and in cell based systems. Specific ADAM 10 modulating peptides are a useful tool to explore how ADAM 10 regulates cellular functions and participates in pathogenesis. ADAM 10 activity has been implicated in diseases such as cancer, neurological disorders, asthma, and allergic responses, and disorders characterized at least in part by the presence of one or more of inflammation, excess cell proliferation, angiogenesis, and excess soluble CD23. The ADAM 10 modulating prodomain peptides of the presently disclosed subject matter have been used in cellular assays to prevent EGF and betacellulin release, CD23 shedding, and tumor cell proliferation in certain cell lines (FIGS. 1-3).

In contrast to the specific ADAM 10 modulating prodomain peptides of the present invention, studies have shown that prodomains of ADAM protein family members do not necessarily inhibit ADAM 10 function. For example, the prodomain of TACE does not inhibit its catalytic/disintegrin containing enzyme even though in vitro studies have shown that the prodomain can inhibit the catalytic domain alone when it is provided as a separate construct (17). In addition, the presently disclosed subject matter discloses that mouse ADAM 8 prodomain does not inhibit mouse ADAM 8 catalytic domain (Table II). Accordingly, the presently disclosed subject matter meets a long-standing need in the art for specific modulators of ADAM 10 activity.

DEFINITIONS

As used herein, the terms "peptide", "polypeptide" and "protein" are used interchangeably to denote a sequence polymer of at least two amino acids covalently linked by an amide bond. The term "homologous" as used herein in reference to peptides, refers to amino acid sequence similarity between two peptides. When an amino acid position in both of the peptides is occupied by identical amino acids, they are homologous at that position. Thus by "substantially homologous" means an amino acid sequence that is largely, but not entirely, homologous, and which retains most or all of the activity as the sequence to which it is homologous. As used herein, "substantially homologous" means that a sequence is at least 95% identical, and preferably at least 98% and more preferably 99% homologous to the reference peptide.

As used herein, the term "polynucleotide" means a sequence of nucleotides connected by phosphodiester linkages. Polynucleotides are presented herein in the direction from the 5' to the 3' direction. A polynucleotide of the presently disclosed subject matter can be a deoxyribonucleic acid (DNA) molecule or ribonucleic acid (RNA) molecule. Where a polynucleotide is a DNA molecule, that molecule can be a gene or a cDNA molecule. Nucleotide bases are indicated herein by a single letter code: adenine (A), guanine (G), thymine (T), cytosine (C), inosine (I) and uracil (U).

In one embodiment, the presently disclosed subject matter provides isolated ADAM 10 modulating peptides. Polypeptides are disclosed herein as amino acid residue sequences. Those sequences are written left to right in the direction from the amino to the carboxyl terminus. In accordance with standard nomenclature, amino acid residue sequences are denominated by either a single letter or a three-letter code as indicated below.

| Amino Acid Residue | 3-Letter Code | 1-Letter Code |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The ADAM 10 modulating peptides of the presently disclosed subject matter include full-length mouse and human ADAM 10 prodomains, and truncations of the prodomain peptides at one or both the N and C terminus. For example, in one embodiment, the ADAM 10 modulating peptides of the presently disclosed subject matter include ADAM 10 modulating peptide comprising an amino acid sequence present in amino acid residues 18-213 of mouse ADAM 10 protein, wherein the peptide has the functionality of specifically modulating ADAM 10 protein activity. In another embodiment of the invention, the ADAM 10 modulating peptides have the functionality of modulating ADAM 10 protein activity and comprise an amino acid sequence present in amino acid residues 18-213 of mouse ADAM 10 protein, wherein the peptides are 154-196 amino acid residues in length and the peptide N-terminus is amino acid residue 18. In a further embodiment of the invention, the ADAM 10 modulating peptides have the functionality of modulating ADAM 10 protein activity and comprise an amino acid sequence present in amino acid residues 23-213 of mouse ADAM 10 protein, wherein the peptides are 154-191 amino acid residues in length and the peptide N-terminus is amino acid residue 23.

In another embodiment, the ADAM 10 modulating peptides of the presently disclosed subject matter include ADAM 10 modulating peptide comprising an amino acid sequence present in amino acid residues 18-212 of human ADAM 10 protein, wherein the peptide has the functionality of specifically modulating ADAM 10 protein activity. In a further embodiment of the invention, the ADAM 10 modulating peptides have the functionality of modulating ADAM 10 protein activity and comprise an amino acid sequence present in amino acid residues 18-212 of human ADAM 10 protein, wherein the peptides are 154-195 amino acid residues in length and the peptide N-terminus is amino acid residue 18. In a further embodiment of the invention, the ADAM 10 modulating peptides have the functionality of modulating ADAM 10 protein activity and comprise an amino acid sequence present in amino acid residues 23-212 of human ADAM 10 protein, wherein the peptides are 154-190 amino acid residues in length and the peptide N-terminus is amino acid residue 23.

The ADAM 10 modulating peptides of the presently disclosed subject matter include amino acid substitutions, for example substitutions such as modifying cysteine 173 of full-length mouse or human ADAM 10 to serine or alanine in the prodomain peptide. Prodomain peptides with such substitutions are useful as they are less susceptible to inactivation due to oxidation of the cysteine residue resulting in disulfide dimerization.

The ADAM 10 modulating peptides of the presently disclosed subject matter include peptides with additional modifications. For example, the ADAM 10 modulating peptides may comprise one or more modifications selected from the group comprising one or more: conservative amino acid substitutions; non-natural amino acid substitutions, D- or D,L-racemic mixture isomer form amino acid substitutions, amino acid chemical substitutions, carboxy- or amino-terminus modifications, and conjugation to biocompatible molecules including fatty acids and PEG. Such modified peptides of the presently disclosed subject matter are described in further detail herein below.

Specific embodiments of the presently disclosed subject matter include the ADAM 10 modulating peptide of SEQ ID NOs 1-8. The ADAM 10 modulating peptide of SEQ ID NO 1 consists of mouse ADAM 10 prodomain amino acid residues 23-213, wherein cysteine 173 of full-length mouse ADAM 10 protein (now 151) may be substituted with serine or alanine. The ADAM 10 modulating peptide of SEQ ID NO 2 consists of mouse ADAM 10 prodomain amino acid residues 23-181, wherein cysteine 173 of full-length mouse ADAM 10 protein (now 151) may be substituted with serine or alanine. The ADAM 10 modulating peptide of SEQ ID NO 3 consists of mouse ADAM 10 prodomain amino acid residues 23-176, wherein cysteine 173 of full-length mouse ADAM 10 protein (now 151) may be substituted with serine or alanine. The ADAM 10 modulating peptide of SEQ ID NO 4 consists of mouse ADAM 10 prodomain amino acid residues 18-176, wherein cysteine 173 of full-length mouse ADAM 10 protein (now 156) may be substituted with serine or alanine. The ADAM 10 modulating peptide of SEQ ID NO 5 consists of human ADAM 10 prodomain amino acid residues 23-212, wherein cysteine 173 of full-length human ADAM 10 protein (now 151) may be substituted with serine or alanine. The ADAM 10 modulating peptide of SEQ ID NO 6 consists of human ADAM 10 prodomain amino acid residues 23-181, wherein cysteine 173 of full-length human ADAM 10 protein (now 151) may be substituted with serine or alanine. The ADAM 10 modulating peptide of SEQ ID NO 7 consists of human ADAM 10 prodomain amino acid residues 23-176, wherein cysteine 173 of full-length human ADAM 10 protein (now 151) may be substituted with serine or alanine. The ADAM 10 modulating peptide of SEQ ID NO 8 consists of human ADAM 10 prodomain amino acid residues 18-176, wherein cysteine 173 of full-length human ADAM 10 protein (now 156) may be substituted with serine or alanine.

The ADAM 10 modulating peptides of the presently disclosed subject matter can include peptides containing sequences on the N or C terminus that are necessary for successful expression of prodomain in *E. coli*, insect cells, or mammalian systems. In addition, tags can be added which aid in the purification of the ADAM 10 modulating peptides of the invention. The tags include, but not limited to, His tags, C-myc tags, Flag tag, HA tag, Streptactin tag, Disulfide tag, and Biotin tag. The sequences between the tag and the prodomain, will usually comprise protease cleavage sites, such as found for enterokinase, thrombin, or Tev proteases. The ADAM 10 modulating peptides of the presently disclosed subject matter may include modifications that stabilize the peptide for in vivo use. Such modifications are generally known to those of skill in the art and include, but are not limited to, modification with fatty acids and pegylation, incorporation of D amino acids, and substitution, deletion, and/or addition of amino acids.

Modifications and changes can be made in the structure of an ADAM 10 modulating peptide of the presently disclosed subject matter and still obtain a molecule having like ADAM 10 modulating properties. For example, certain amino acids can be substituted for other amino acids in a sequence without appreciable loss of peptide activity. Because it is the interactive capacity and nature of a polypeptide that defines that polypeptide's biological functional activity, certain amino acid sequence substitutions can be made in a polypeptide sequence (or, of course, its underlying DNA coding sequence) and nevertheless obtain a polypeptide with like properties.

In making such changes, the hydropathic index of amino acids can be considered. The importance of the hydropathic amino acid index in conferring interactive biologic function on a polypeptide is generally understood in the art (20). It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those which are within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments.

U.S. Pat. No. 4,554,101, incorporated herein by reference, states that the greatest local average hydrophilicity of a polypeptide, as governed by the hydrophilicity of its adjacent amino acids, correlates with its immunogenicity and antigenicity, i.e. with a biological property of the polypeptide. As detailed in U.S. Pat. No. 4,554,101, the following hydrophilicity values have been assigned to amino acid residues: arginine (+3.0); lysine (+3.0); aspartate (+3.0.+−0.1); glutamate (+3.0.+−0.1); serine (+0.3); asparagine (+0.2); glutamine (+0.2); glycine (0); proline (−0.5.+−0.1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine (See Table 1, below). The presently disclosed subject matter thus contemplates functional or biological equivalents of a peptide as set forth above.

TABLE 1

| Original Residue | Exemplary Substitutions |
| --- | --- |
| Ala | Gly; Ser |
| Arg | Lys |
| Asn | Gln; His |
| Asp | Glu |
| Cys | Ser |
| Gln | Asn |
| Glu | Asp |
| Gly | Ala |
| His | Asn; Gln |
| Ile | Leu; Val |
| Leu | Ile; Val |
| Lys | Arg |
| Met | Leu; Tyr |
| Ser | Thr |
| Thr | Ser |
| Trp | Tyr |
| Tyr | Trp; Phe |
| Val | Ile; Leu |

Biological or functional equivalents of a polypeptide can be prepared using site-specific mutagenesis according to procedures well known in the art. Accordingly, amino acid residues can be added to or deleted from the ADAM 10 modulating peptides of the presently disclosed subject matter through the use of standard molecular biological techniques without altering the functionality of the peptide. Specific examples include the various truncated mouse and human ADAM 10 prodomain peptides and the cysteine to serine substituted prodomain peptides of the presently disclosed subject matter.

A polypeptide of the presently disclosed subject matter is prepared by standard techniques well known to those skilled in the art. Such techniques include, but are not limited to, isolation and purification from tissues known to contain that polypeptide, and expression from cloned DNA that encodes such a polypeptide using transformed cells.

In one aspect, the presently disclosed subject matter provides an isolated polynucleotide that encodes an ADAM 10 modulating peptide of the invention.

In one embodiment, the polynucleotide of the presently disclosed subject matter encodes a polypeptide comprising the amino acid sequence selected from SEQ ID NOs 1-8. A polynucleotide of the presently disclosed subject matter can be prepared using any of the standard techniques well known to one of skill in the art. See *Cloning of ADAM family cDNA* herein at the EXAMPLES for one such standard technique.

In one embodiment, the presently disclosed subject matter provides an expression vector comprising a polynucleotide encoding an ADAM 10 modulating peptide of the invention. In a specific embodiment, expression vectors of the presently disclosed subject matter comprise polynucleotides that encode polypeptides comprising the amino acid residue sequence of SEQ ID NOs: 1-8. In another aspect, expression vectors of the presently disclosed subject matter comprise polynucleotides operatively linked to an enhancer-promoter. In yet another embodiment, expression vectors of the presently disclosed subject matter comprise a polynucleotide operatively linked to a prokaryotic or eukaryotic promoter.

An expression vector of the presently disclosed subject matter is useful for preparing quantities of the ADAM 10 modulating peptide-encoding DNA itself, and for preparing the encoded peptides. It is provided that where ADAM 10 modulating peptides of the presently disclosed subject matter are made by recombinant approaches, one can employ either prokaryotic or eukaryotic expression vectors as shuttle systems according to methods well known in the art.

In yet another embodiment, the presently disclosed subject matter provides recombinant host cells transformed or transfected with a polynucleotide that encodes an ADAM 10 modulating peptide of the invention, as well as transgenic cells derived from those transformed or transfected cells. In a specific embodiment, recombinant host cells of the presently disclosed subject matter are transfected with a polynucleotide that encodes for a peptide having an amino acid residue sequence selected from SEQ ID NOs 1-8. Approaches for transforming or transfecting cells with exogenous polynucleotide such as DNA molecules are well known in the art and include techniques such as calcium-phosphate- or DEAE-dextran-mediated transfection, protoplast fusion, electroporation, liposome mediated transfection, direct microinjection, and adenovirus infection.

A transfected cell can be prokaryotic or eukaryotic. In one embodiment, the recombinant host cells of the presently disclosed subject matter are prokaryotic host cells. Preferably, the recombinant host cells of the presently disclosed subject matter are bacterial cells of the DH5α strain of *Escherichia coli*. In general, prokaryotes are preferred for the initial cloning of DNA sequences and constructing the vectors useful in the invention. For example, *E. coil* K12 strains can be particularly useful. Other microbial strains which can be used include *E. coli* B, and *E. coli* X1776 (ATCC No. 31537). These examples are, of course, intended to be illustrative rather than limiting.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* can be transformed using pBR322, a plasmid derived from an *E. coli* species. pBR322 contains genes for ampicillin and tetracycline resistance and thus provides an easy approach for identifying transformed cells. The pBR plasmid, or other microbial plasmid or phage must also contain, or be modified to contain, promoters which can be used by the microbial organism for expression of its own polypeptides.

Those promoters most commonly used in recombinant DNA construction include the beta-lactamase (penicillinase) and lactose promoter systems and a tryptophan (TRP) promoter system. While these are the most commonly used, other microbial promoters have been discovered and utilized, and details concerning their nucleotide sequences have been published, enabling a skilled worker to introduce functional promoters into plasmid vectors.

In another embodiment, the recombinant host cells of the presently disclosed subject matter are eukaryotic host cells. *Saccharomyces cerevisiae* or common baker's yeast is the most commonly used among eukaryotic microorganisms, although a number of other strains are commonly available. For expression in *Saccharomyces*, the plasmid YRp7, for example, is commonly used. This plasmid already contains the trpl gene, which provides a selection marker for a mutant strain of yeast lacking the ability to grow in tryptophan, for example ATCC No. 44076 or PEP4-1. The presence of the trpl lesion as a characteristic of the yeast host cell genome then provides an effective environment for detecting transformation by growth in the absence of tryptophan. Suitable promoter sequences in yeast vectors include the promoters for 3-phosphoglycerate kinase or other glycolytic enzymes such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also introduced into the expression vector downstream from the sequences to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin or replication and termination sequences is suitable.

In addition to microorganisms, cultures of cells derived from multicellular organisms can also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years. Examples of such useful host cell lines are AtT-20, VERO and HeLa cells, Chinese hamster ovary (CHO) cell lines, and W138, BHK, COSM6, COS-1, COS-7, 293 and MDCK cell lines. Expression vectors for such cells ordinarily include (if necessary) an origin of replication, a promoter located upstream of the gene to be expressed, along with any necessary ribosome binding sites, RNA splice sites, polyadenylation site, and transcriptional terminator sequences.

For use in mammalian cells, the control functions on the expression vectors are often derived from viral material. For example, commonly used promoters are derived from polyoma, Adenovirus 2, Cytomegalovirus and most frequently Simian Virus 40 (SV40). The early and late promoters of SV40 virus are particularly useful because both are obtained easily from the virus as a fragment, which also contains the SV40 viral origin of replication. Smaller or larger SV40 fragments can also be used, provided there is included the approximately 250 bp sequence extending from the HindIII site toward the BgII site located in the viral origin of replication. Further, it is also possible, and often desirable, to utilize promoter or control sequences normally associated with the desired gene sequence, provided such control sequences are compatible with the host cell systems.

In one embodiment, the presently disclosed subject matter provides a process for preparing an ADAM 10 modulating peptide of the presently disclosed subject matter comprising transforming or transfecting cells with a polynucleotide that encodes an ADAM 10 modulating peptide to produce transformed host cells; and maintaining the transformed host cells under biological conditions sufficient for expression of the polypeptide. The type of host cell used in the process is capable of expressing functional, recombinant ADAM 10 modulating peptide. A variety of cells are amenable to this process of the invention, for instance, bacterial cells, Chinese hamster ovary cells, yeasts cells, human cell lines, and other prokaryotic and eukaryotic cell lines known well to those of the art.

Following transfection, the cell is maintained under culture conditions for a period of time sufficient for expression of an ADAM 10 modulating peptide. Culture conditions are well known in the art and include ionic composition and concentration, temperature, pH and the like. Typically, transfected cells are maintained under culture conditions in a culture medium. Suitable medium for various cell types are well known in the art. In a preferred embodiment, temperature is from about 20° C. to about 50° C. Other biological conditions needed for transfection and expression of an encoded protein are well known in the art. Transfected cells are maintained for a period of time sufficient for expression of an ADAM 10 modulating peptide. A suitable time depends inter alia upon the cell type used and is readily determinable by a skilled artisan.

A recombinant VID peptide is recovered or collected either from the transfected cells or the medium in which those cells are cultured. Recovery comprises isolating the recombinant polypeptide. Isolation techniques for polypeptides are well known in the art and include such procedures as precipitation, filtration, chromatography, electrophoresis and the like.

In one embodiment, the presently disclosed subject matter provides pharmaceutical compositions comprising an ADAM 10 modulating peptide and a physiologically acceptable carrier. In a specific embodiment, the pharmaceutical composition comprises an ADAM 10 modulating peptide having the amino acid residue sequence of SEQ ID NOs: 1-8.

A composition of the presently disclosed subject matter is typically administered parenterally in dosage unit formulations containing standard, well-known nontoxic physiologically acceptable carriers, adjuvants, and vehicles as desired. The term parenteral as used herein includes intravenous, intramuscular, intraarterial injection, or infusion techniques.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables. Preferred carriers include neutral saline solutions buffered with phosphate, lactate, Tris, and the like.

The compositions of the presently disclosed subject matter include vectors that comprise a polynucleotide encoding an ADAM 10 modulating peptide of the invention. One purifies the vector sufficiently to render it essentially free of undesirable contaminants, such as defective interfering adenovirus particles or endotoxins and other pyrogens such that it does not cause any untoward reactions in the individual receiving the vector construct. A transfected cell can also serve as a carrier. By way of example, a liver cell can be removed from an organism, transfected with a polynucleotide of the presently disclosed subject matter using methods set forth above and then the transfected cell returned to the organism (e.g. injected intravascularly).

The ADAM 10 modulating peptides of the presently disclosed subject matter are useful for modulating ADAM 10 protein activity in vitro and in vivo. In one embodiment, the presently disclosed subject matter provides a method for modulating ADAM 10 activity in vitro: comprising contacting an ADAM 10 modulating prodomain with a solution or a cell comprising ADAM 10 protein, wherein the amount of the contacted prodomain is sufficient to modulate the activity of the ADAM 10 protein. In another embodiment, the presently disclosed subject matter provides a method for modulating ADAM 10 activity in vivo, the method comprising administering to an animal a composition or pharmaceutical formulation comprising an ADAM 10 modulating prodomain in an amount sufficient to modulate ADAM 10 activity. In one aspect, the animal has a disorder characterized at least in part by the presence of an excess of ADAM 10 activity. In another aspect, the disorder is characterized by one or more of inflammation, allergic response, asthma, angiogenesis, cancer, or a predisposition to such disorder. In another aspect, the animal has a disorder characterized at least in part by being deficient in ADAM 10 activity. In another aspect, the disorder is characterized by one or more of a neurological disorder, dementia, Alzheimer's, or a predisposition to such disorder.

In one embodiment, the prodomain is an ADAM 10 modulating peptide comprising an amino acid sequence present in amino acid residues 18-213 of mouse ADAM 10 protein. In another embodiment, the prodomain is an ADAM 10 modulating peptide consisting of an amino acid sequence present in amino acid residues 18-213 of mouse ADAM 10 protein. In another embodiment, the prodomain is an ADAM 10 modulating peptide comprising an amino acid sequence present in amino acid residues 18-212 of human ADAM 10 protein. In another embodiment, the prodomain is an ADAM 10 modulating peptide consisting of an amino acid sequence present in amino acid residues 18-212 of human ADAM 10 protein. In another embodiment, the ADAM 10 modulating prodomain comprises SEQ ID NO 1, SEQ ID NO 2, SEQ ID NO 3, SEQ ID NO 4, SEQ ID NO 5, SEQ ID NO 6, SEQ ID NO 7, or SEQ ID NO 8, or an ADAM 10 modulating peptide having at least 95% homology to SEQ ID NO 1, SEQ ID NO 2, SEQ ID NO 3, SEQ ID NO 4, SEQ ID NO 5, SEQ ID NO 6, SEQ ID NO 7, or SEQ ID NO 8.

In another embodiment, the presently disclosed subject matter provides a method for decreasing the generation of soluble CD23 in a cell-based assay or in an animal, the method comprising administering to the cells or animal a composition or pharmaceutical formulation comprising an ADAM 10 modulating prodomain in an amount sufficient to decrease the level of soluble CD23. In one aspect, the cells or the animal have or are derived from an animal having a disorder characterized at least in part by the presence of an excess of soluble CD23. In another aspect, the disorder is characterized by one or more of inflammation, allergic response, asthma, or a predisposition to such disorder.

In another embodiment, the presently disclosed subject matter provides a method for decreasing inflammation, the method comprising administering to an animal a composition or pharmaceutical formulation comprising an ADAM 10 modulating prodomain in an amount sufficient to decrease inflammation in the animal. In one aspect, the animal has a disorder characterized at least in part by the presence of excess inflammation. In another aspect, the disorder is characterized by one or more of inflammation, allergic response, asthma, angiogenesis, cancer, or a predisposition to such disorder.

In another embodiment, the presently disclosed subject matter provides a method for inhibiting cell proliferation, the method comprising administering to a cell-based assay or an animal a composition or pharmaceutical formulation comprising an ADAM 10 modulating prodomain in an amount sufficient to decrease cell proliferation in the cells or the animal. In one aspect the animal has a disorder characterized at least in part by the presence of excess cell proliferation. In another aspect, the disorder is characterized by one or more of inflammation, allergic response, asthma, angiogenesis, cancer, or a predisposition to such disorder.

EXAMPLES

Materials. Human ADAM10, ADAM9, and TACE protease containing the catalytic/disintegrin domains were obtained from R & D Systems (Minneapolis, Minn., USA). The following enzymes were generously donated: TACE catalytic domain, Marcos Milla, University of Pennsylvania; MMP 1 and 3, Hideaki Nagase, Imperial College London; MMP 2 and 9, William Stetler-Stevenson, National Cancer Institute; MMP 13 and 14, Gillian Murphy, Cambridge University. All fluorescent labeled peptides were purchased from SynPep Corp. (Dublin, Calif., USA). Dinitrophenyl labeled peptides were purchased from the UNC Chapel Hill peptide synthesis laboratory. All oligos for PCR and directed mutagenesis were ordered from IDT DNA (Coralville, Iowa, USA).

Cloning of ADAM family cDNA. A DNA fragment containing ADAM 10 prodomain (23-213) was cloned into the pRSET vector (Invitrogen Corporation, Carlsbad, Calif.) between BamHI and EcoRI sites to produce a N-terminal His-tagged protein, or cloned into a modified pET30a vector (EMD Biosciences, Madison, Wis.) between NdeI and BamHI sites as a C-terminal His-tagged protein. The modified pET30a vector encodes His6 between BamHI and EcoRI sites to produce a protein with a C-terminal His-tag. DNA primers were: N-His (23-213) 5' primer: GGA GCC GGA TCC AAT CCT TTA AAT AAA TAT ATT (SEQ ID NO 9), 3' primer: GGA GCC GAA TTC TTA GCG TTT TTT CCT CAG GAG CTC (SEQ ID NO 10); C-His (23-213) 5' primer: GGA GCC CAT ATG AAT CCT TTA AAT AAA TAT ATT (SEQ ID NO 11), 3' primer: GGA GCC GGA TCC TTT TTT CCT CAG GAG CTC AGG (SEQ ID NO 12); and C-His (23-181) 5' primer: GGA GCC CAT ATG AAT CCT TTA AAT AAA TAT ATT (SEQ ID NO 13), 3' primer: GGA GCC GGA TCC TTC AAA AAC GGA GTG ATC (SEQ ID NO 14). The wild type 23-213 C-His ADAM 10 prodomain was used as a template to mutate cysteine 173 to serine. The DNA primers for site-directed mutagenesis were: 5' primer: AAA TAC GGC CCA CAG GGC GGC TCT GCA GAT CAC TCC GTT TTT GAA (SEQ ID NO 15), 3' primer: TTC AAA AAC GGA GTG ATC TG AGA GCC CC CTG GG GCC GTA TTT (SEQ ID NO 16).

For prodomains of TACE (18-214) and ADAM 8 (18-186), mouse full length cDNAs were used as templates to prepare fragments that were subcloned into the same vector as described for ADAM 10.

Expression and purification. The foregoing constructs were transformed into E. coli BL21(DE3)STAR cells. For a typical sample preparation, bacteria were grown in 1 liter of luria broth at 37° C. until the $OD_{600}$ reached 0.4. The culture was incubated at 20° C. for 30 min before adding IPTG (1 mM) to induce protein expression. Cells were harvested after 16 hours by spinning at 4° C. for 30 min at 4000 rpm in a Sorvall JA 10 rotor. The supernatant was removed and pellets were either stored at −20° C. or used directly.

Cell pellets were lysed by French Press at 1100 psi in 25 ml of buffer containing 50 mM phosphate, pH 8.0, 10 mM imidazole, and 300 mM NaCl at 4° C. or lysed with the same buffer with cell lytic (3 ml of a 10× concentrated solution), benzonase, 1500 units, and lysozyme (0.2 mg/ml). For the wild type constructs, 0.1% beta mercaptoethanol was added to each buffer to minimize oxidation of cysteine. Lysed bacteria were spun at 21,500 rpm in a Beckman JA 25.50 rotor for 30-60 minutes. The cleared supernatant was applied to a 15 ml $Ni^{2+}$-NTA column pre-equilibrated with lysis buffer. After two 30 ml washes with a solution containing 50 mM phosphate, pH 8.0, 20 mM imidazole, and 300 mM NaCl, the protein was eluted with a solution containing 50 mM phosphate, pH 8.0, 250 mM imidazole, and 300 mM NaCl. The eluted protein was concentrated to less than 2 ml using an Amicon ultra filtration device (molecular weight cutoff 10 kDa) from Millipore (Billerica, Mass.) and further purified with a Superdex-75 column (150 ml) on an Akta FPLC system at a flow rate of 1 ml/min. FPLC buffers contained 25 mM phosphate, pH 7.0, 100 mM NaCl or 25 mM Tris, pH 8.0, 100 mM NaCl. Fractions containing protein were concentrated and stored either at 4° C. or as glycerol stocks at −80° C.

Ultracentrifugation. The molecular weight of ADAM 10 prodomain in 25 mM phosphate, pH 7.0, 150 mM KCl, was estimated by sedimentation equilibrium at 15000 and 20000 rpm and at 25° C. on a Beckman Model XL-A analytical Ultracentrifuge. The V(bar) of the protein and ρ of the solvent were estimated to be 0.7216 and 1.005 respectively by the SEDNTRP program. The protein was examined at several concentrations (0.45, 0.9, and 1.8 mg/mL) and was monitored by the absorbance at 286 nm. The non-linear least square curve was generated by the IDEALI program (Beckman).

Circular Dichroism (CD) spectroscopy. A 30 μM sample of the 23-213 ADAM 10 construct in a buffer containing 25 mM phosphate and 50 mM NaCl, pH 8.0 was used to obtain a CD spectrum on an Aviv 202 CD spectrometer. A wavelength scan from 200 to 300 nm was collected in a 1 mm quartz cuvette at 25° C. Scans were obtained in 1 nm increments with a signal averaging time of 5 s. Background noises from the buffer were subtracted from the raw CD signal.

Inhibition assays with TACE and ADAM 10. Activity of TACE catalytic/disintegrin, TACE catalytic, or ADAM10 catalytic/disintegrin constructs was monitored at 3 minute intervals using the fluorescent substrate, Dabcyl-LAQAHomoPheRSC(Fluorescein)-$NH_2$ (SEQ ID NO 17) with excitation 485 nm and emission 530 nm. The substrate was diluted from a 10 mM stock in DMSO to 10 μM in assay buffer containing 20 mM Tris, pH 8.0, and 0.0006% Brij-35. Reactions were run in a 96-well black-coated plate with either ADAM10 prodomain (10 nM-1.0 µM) alone or with enzyme. Concentrations of enzyme ranged from 0.5-2.0 nM for TACE and 5-15 nM for ADAM10. For assays with TACE and ADAM8 prodomain, the range of concentrations varied from 1-4.7 µM.

Inhibition assays with MMPs. The fluorescent substrate Dabcyl-GPLGMRGC (Fluorescein)-NH$_2$ (SEQ ID NO 18) (10 µM) in assay buffer containing 50 mM Tris, pH 7.5, 150 mM NaCl, 2 mM CaCl$_2$, 5 µM ZnSO$_4$, and 0.01% Brij-35 was used to monitor enzyme activities. MMPs 1, 2, 3, 9, 13, and 14 (0.1-20 nM) were incubated with substrate in the absence or presence of prodomain (3-30 µM). Fluorescence intensities were measured every 3-5 minutes at an emission wavelength of 530 nm (excitation 485 nm).

Inhibition assays with ADAM 9. The fluorescent substrate, Dabcyl-PchaGC(Me)HAK(Fam)-NH$_2$ (SEQ ID NO 19) (10 µM), in a buffer containing 25 mM Tris, pH 8.0, 0.0006% Brij-35, was used to measure human ADAM 9 catalytic/disintegrin domains activity. The ADAM 9 was provided as a 0.1 µg/µl stock solution, from which 3 µl was added to start the reaction in the absence or presence of ADAM10 prodomain (78-5000 nM). Fluorescence intensities were measured every 10-20 minutes at excitation and emission wavelengths of 485 and 530 nm respectively.

Inhibition assays with ADAM 8. The ADAM 8 catalytic domain was expressed and purified from *E. coli* as described (22). A substrate based on the L-selectin cleavage site, Dnp-INorIeuQKLDKSFSMIKE-NH$_2$ (SEQ ID NO 20), was used to monitor enzyme activity with a fluorescamine assay. From a concentrated 50 mM solution in DMSO, the substrate was diluted 1:500 in 25 mM HEPES, pH 8.0, 0.0006% Brij-35. To 100 µl of diluted substrate was added either 5 µl of buffer (Tris, pH 8.0, 150 mM KCl) or 5 µl of ADAM10 prodomain (1-10 µM). Zero time points were taken by diluting 12.5 µl of the reaction mixture into 100 µl of fluorescamine buffer (50 mM HEPES, pH 8.0, 0.2 M NaCl, 0.01 M CaCl$_2$, 0.01% Brij-35) in a 96-well black-coated plate. Before measuring fluorescence, 3 µl of a 1% solution of fluorescamine in DMSO was added to each well. The plate was allowed to incubate for 10 min in the dark before measuring fluorescence (excitation wavelength at 390 nm, emission wavelength at 485 nm). For assays with TACE and ADAM8 prodomains, a fluorescent substrate was used to monitor activity at concentrations of prodomains ranging from 1-4.7 µM.

Calculation of inhibition constants. The amount of activity was calculated by subtracting the ADAM 10 prodomain control from the ADAM 10 prodomain with enzyme. All inhibition assays were performed at room temperature and the data fit to the following equation using Sigma Plot software:

$$I_f = \frac{I}{(I + K_i)} \quad (1)$$

where $I_f$ is fractional inhibition, I is the inhibitor concentration and $K_i$ is the inhibition constant.

Mechanism of ADAM 10 prodomain inhibition. For metalloproteinases that exist as zymogens, the presence of a cysteine in their prodomains is often necessary for inhibition of catalytic activity. The cysteine is proposed to chelate the active site zinc ion of the metalloproteinase, causing the enzyme to remain in an inactive state. For some of the ADAM family members, the cysteine is required for efficient inhibition of the enzyme. Therefore, a test was conducted to determine whether the cysteine in the putative cysteine switch of ADAM10 prodomain affected the potency of inhibition by preparing a C-terminal His tag construct with the only cysteine mutated to serine. The C173S ADAM 10 prodomain (23-213) was found to be a tight and specific inhibitor of human ADAM 10 with an inhibition constant of 36±9 nM (Table II). Furthermore, mouse ADAM 10 catalytic domain (unpublished observation) is inhibited with a $K_i$ of 17±10 nM, supporting the hypothesis that there are no species differences that account for the potency of ADAM10 prodomain. These results indicate that the cysteine residue in the ADAM10 prodomain is not required for efficient inhibition of catalytic activity and the inhibitory mechanism of ADAM 10 prodomain is distinct from the cysteine switch mechanism. The wild type prodomains (23-213), containing either the N- or C-terminal His tags, were both efficient inhibitors of ADAM10 (Table II), with inhibition constants of 75 and 48 nM respectively. It was therefore concluded that ADAM 10 prodomain inhibition of ADAM 10 does not depend on the location of the His tag.

Wild type ADAM 10 prodomain (23-213) was tested to determine the mode of inhibition of ADAM 10 protein. ADAM 10 protein was diluted 1:100 in buffer 25 mM Tris pH 8, 0.0006% Brij-35 and then 10 µl was added to 88 µl of substrate (20-100 µM), Dabcyl-LAQAHomoPheRSC(Fluorescein)-NH$_2$ with excitation 485 nm and emission 530 nm. Prodomain, 2 µl, in 25 mM Tris, pH 8, 100 mM NaCl, 10% glycerol, 0.1% mercaptoethanol, and 50 µM CaCl$_2$ was added to substrate before addition of enzyme. The final concentration of prodomain ranged from 17-170 nM. The fluorescence vs time was plotted, and slopes were taken from straight line fits of initial velocities. The reciprocal of the velocities was plotted vs the reciprocal of substrate squared since the normal Lineweaver Burke plot gave curved lines. The initial velocities vs substrate concentrations were fit as a family of curves to several allosteric models. The data fit best to a pure competitive model as described in the following equation where binding of inhibitor prevents substrate from binding to both sites:

$$v = V^*((S/K_s) + (S^2/K_s^2))/(1 + (2^*S/K_s) + (X^2/K_s^2) + (I/K_i))$$

The $K_i$, calculated with this method was 48±36 nM and the binding constant, $K_s$ for substrate was 16±4.6 µM (Table II).

Further inhibition studies were carried out against ADAM and MMP family members to evaluate the specificity of ADAM 10 prodomain (Table II). The ADAM 10 prodomain constructs inhibited ADAM 10 with inhibition constants in the nanomolar range. In contrast, the closely related family members, matrix metalloproteinases 1, 2, 3, 9, 13 and 14, were not inhibited by 3 µM mouse wild type ADAM 10 prodomain (residues 23-213) containing either a N-terminal or a C-terminal His tag, or 3 µM mouse C173S ADAM 10 prodomain (residues 23-213) containing a C-terminal His tag (Table II). In addition, TACE catalytic and TACE catalytic/disintegrin enzymes were inhibited only slightly by the foregoing prodomain constructs at concentrations of ~30 µM. Some inhibition of ADAM 8 was seen between 4 and 9 µM, and ADAM 9 was inhibited with a $K_i$ near 1 µM. Inhibition of ADAM 10 by its prodomain seems to be unique, as the prodomains of TACE and ADAM 8 did not inhibit their respective enzymes at micromolar concentrations (Table III).

TABLE II

Inhibitory properties of mouse ADAM 10 prodomain (23-213)

| | Enzyme | | | | | |
|---|---|---|---|---|---|---|
| Inhibitor | ADAM 10 (human) Cat/Dis[+] | TACE (human) Cat/Dis[+] | TACE (human) Cat[+] | ADAM 8 (mouse) | ADAM 9 (human) | MMP 1, 2, 3, 9, 13, 14 |
| wt ProADAM 10 23-213* (N-terminal His tag) | 75 ± 15 nM | >3 μM | >11 μM | ND | ND | >2 μM |
| wt ProADAM 10 23-213* (C-terminal His tag) | 48 ± 36 nM | >10 μM | >11 μM | >10 μM | >1 μM | >2 μM |
| C173S ProADAM 10 23-213* (C-terminal His tag) | 36 ± 9 nM | >3 μM | >3 μM | >10 μM | >1 μM | >2 μM |

[+]'Cat' represents catalytic domain and 'Dis' represents disintegrin domain.
*'23-213' represents amino acids 23-213 of mouse ADAM 10 protein.

TABLE III

ADAM 17 and ADAM 8 prodomain inhibition of various ADAM family members.

| | Enzyme | | | |
|---|---|---|---|---|
| Inhibitor | TACE (human) Cat/Dis[+] | TACE (human) Cat[+] | ADAM 10 (human) Cat/Dis[+] | ADAM 8 (mouse) Cat[+] |
| Pro ADAM 17 (mouse) | 0% at 3.5 μM | 37% at 3.5 μM | 11% at 3.5 μM | 17% at 1.7 μM |
| Pro ADAM 8 (mouse) | 13% at 3 μM | 50% at 3 μM | 25% at 3 μM | 9% at 3 μM |

[+]'Cat' represents catalytic domain and 'Dis' represents disintigrin domain.

ADAM 10 Prodomain Inhibition of Tumor Cell Proliferation

FIG. 1

The question of whether ADAM 10 prodomain could be used in cellular assays to affect ADAM 10 function was tested. Specifically whether wild type ADAM 10 prodomain (23-213) would be able to inhibit tumor cell proliferation in two bladder cancer cells lines, BV 253 and KU-7. To perform the experiment, cells (BV253 or KU-7) were plated at 5,000 cells per well in a 96-well plate in 10% MEM (minimal essential media). The following day, the media was changed to 3% MEM for an overnight serum starvation. After serum starvation, treatment began in 3% MEM with prodomain of ADAM 10 at concentrations of 0, 1.7, and 5 μM. After 48 hours, the supernatant was removed and replaced with tritiated thymidine (3H-TdR) at 5 μCi/ml of media and allowed to incubate for a period of 2 hours. After incubation, the radioactive supernatant was harvested and replaced with 100 μL of 0.1 M KOH. The plate contents were harvested utilizing the beta-plate machine onto filter mats, which were placed into a beta-plate reader to interpret the relative counts of radioactivity per well.

The results indicate that the various ADAM 10 prodomains were able to inhibit tumor cell proliferation in the two bladder cancer cells lines, BV 253 and KU-7 (FIG. 1). The inhibition was independent of the cells responsiveness to an EGF receptor neutralizing antibody, IM 225 (21).

ADAM 10 Inhibition of CD23 Release from U937 and Ramos Cells

FIGS. 2A and 2B

ADAM 10 prodomains were also tested in assays to determine if ADAM 10 protein functions as a CD23 sheddase. Cells (100,000 per well) were seeded in round-bottomed 96-well plates (Sarstedt, Newton, N.C.) in 0.2 ml of media supplemented with IL-4 with inhibitors (A10 23-215 150-600 nM, GM6001 10-50 μM, TAPI-2 10-50 μM, or TIMPs 250 nM) or vehicle controls (A10 23-215 buffer: 25 mM $NaH_2PO_4$ pH 7.0, 125 mM KCl, 75 mM NaCl 20% glycerol, PBS, or dimethyl sulfoxide). Cells were cultured for 24 hr. The conditioned medium was harvested by centrifugation (2000×g, 15 min). The conditioned medium was assayed by ELISA for soluble CD23 according to the manufacturers' instructions (BD Biosciences, Invitrogen).

The results are shown in FIGS. 2A and 2B. C173S ADAM 10 prodomain inhibited about 30% of CD23 shedding in Ramos and U937 cells.

ADAM 10 Inhibition of Shedding in B Cells

FIGS. 2C and 2D

The CD23 sheddase activity of ADAM 10 protein was further tested in a B-cell assay. B-cells were cultured for 12 hr in the presence or absence of IL-4 (100 ng/ml), wild type C-terminal His tagged ADAM 10 (23-213) (1-5 μM) or match diluent control (25 mM Tris-HCl pH 8, 100 mM NaCl, 10% glycerol, 0.1% β-mercaptoethanol). Cells were stained for expression of surface antigens following washing with 1% BSA/PBS. Cells were incubated for 30 minutes at 4° C. in the dark with fluorochrome-conjugated mAbs: APC-CD19 (CALTAG, Burlingame, Calif.), CD23-PE, mIgG1-PE (BD Biosciences) before washing to remove unbound mAb. Cells were resuspended in PBS and immediately analyzed with the use of the FACS Calibur (BD Biosciences). The software program FlowJo (Ashland, Oreg.) was used to analyze data generated by flow cytometry.

FIG. 2 shows that wild type ADAM 10 prodomain (23-213) is able to inhibit shedding in B cells (panel C) and in B cells stimulated with IL-4 (panel D).

ADAM 10 Inhibition of Betacellulin Shedding

FIG. 3

One way in which cancer cells proliferate, is through activation of the EGF receptor by EGF ligand family members. A therapeutic method currently being investigated for bladder cancer is through the use of EGFR neutralizing antibodies, as they are able to block binding to EGFR by EGF ligand. Because ADAM 10 is a processing enzyme for EGF and betacellulin and because the prodomain of ADAM 10 is a specific inhibitor of the human ADAM 10, it was reasoned that the ADAM 10 prodomain should be able to prevent release of EGF ligands in cell based assays.

The conditionally-immortalized pancreatic epithelial (IMPE) cell line was stably transduced with the retrovirus pBM BTC-HA IRES Puro expressing human BTC cDNA with a C-terminal HA-tag as previously described (23). Cells were routinely cultured at 33° C. in Dulbecco's modified Eagle's medium (DMEM) plus 5% bovine growth serum/penicillin/streptomycin/nonessential amino acids and 5 units/ml IFNγ. For BTC shedding assay, cells were seeded at 1×10$^5$ cells/well in 6-well plates and grown for 48 h to confluence at 33° C. in medium containing IFNγ and then for an additional 36 h at 37° C. in medium lacking IFNγ. For all shedding assays, cells were pretreated for 30 min at 37° C. with serum-free DMEM containing vehicle control (DMSO), 50 µM GM6001, or different concentrations of either buffer control or ADAM10 prodomain. For analysis of constitutive BTC shedding, media was then replaced with fresh media using the same experimental treatments and incubated for 4 h at 37° C. To evaluate ionophore-stimulated BTC shedding, media was then replaced with fresh media using the same experimental treatments containing 2 µM A23187 and incubated for 1 h at 37° C. Conditioned media (CM) and cell lysates were then harvested as previously described (23). A specific human BTC sandwich ELISA (R&D Systems) was used to quantify BTC levels in CM and cell lysates according to the manufacturer's instructions. The recombinant human BTC ectodomain (R&D Systems) was used as a standard. All experiments were repeated at least three times with similar results, and a representative figure is presented (FIG. 3). Values for each experiment are expressed as the means±SEM of triplicate determinations.

The prodomain of ADAM 10 was able to inhibit both constitutive (FIG. 3A left two panels) and calcium ionophore induced betacellulin release (FIG. 3A right two panels) in a dose response fashion. Inhibition of constitutive shedding was observed at 15 and 1.5 µM, reaching 90% and 75% inhibition, respectively. Calcium ionophore induced shedding was reduced less by prodomain, with 67% inhibition at 15 µM and 25% inhibition at 1.5 µM. In contrast to the betacellulin assay, no inhibition of amphiregulin was seen with prodomain. Amphiregulin is another EGF ligand family member, but it is known to be cleaved by TACE and not ADAM 10. These results confirm that the prodomain is highly specific for ADAM 10 as only betacellulin and not amphiregulin shedding is prevented.

REFERENCES

The contents of references cited herein are incorporated by reference herein for all purposes:

1. Wolfsberg T G, Straight P D, Gerena R L, Huovila A P, Primakoff P, Myles D G, White J M. ADAM, a widely distributed and developmentally regulated gene family encoding membrane proteins with a disintegrin and metalloprotease domain. *Dev Biol.* 1995; 169(1):378-83
2. Moss, M. L., and Bartsch, J. W. Therapeutic benefits from targeting of ADAM family members. *Biochemistry* 2004; 43, 7227-35.
3. Blobel, C. P. ADAMs: key components in EGFR signalling and development. *Nat Rev Mol Cell Biol.* 2005; 6, 32-43.
4. Pan D, Rubin G M. Kuzbanian controls proteolytic processing of Notch and mediates lateral inhibition during *Drosophila* and vertebrate neurogenesis. *Cell* 1997; 90(2): 271-80.
5. Lammich S, Kojro E, Postina R, Gilbert S, Pfeiffer R, Jasionowski M, Haass C, Fahrenholz F. Constitutive and regulated alpha-secretase cleavage of Alzheimer's amyloid precursor protein by a disintegrin metalloprotease. *Proc Natl Acad Sci USA* 1999; 96(7):3922-7.
6. Janes P W, Saha N, Barton W A, Kolev M V, Wimmer-Kleikamp S H, Nievergall E, Blobel C P, Himanen J P, Lackmann M, Nikolov D B. Adam meets Eph: an ADAM substrate recognition module acts as a molecular switch for ephrin cleavage in trans. *Cell* 2005; 123(2):291-304.
7. Maretzky T, Reiss K, Ludwig A, Buchholz J, Scholz F, Proksch E, de Strooper B, Hartmann D, Saftig P. ADAM10 mediates E-cadherin shedding and regulates epithelial cell-cell adhesion, migration, and beta-catenin translocation. *Proc. Natl. Acad. Sci. USA* 2005; 102(26):9182-7.
8. Reiss K, Maretzky T, Ludwig A, Tousseyn T, de Strooper B, Hartmann D, Saftig P. ADAM10 cleavage of N-cadherin and regulation of cell-cell adhesion and beta-catenin nuclear signalling. *EMBO J.* 2005; 24(4):742-52.
9. Ludwig A, Hundhausen C, Lambert M H, Broadway N, Andrews R C, Bickett D M, Leesnitzer M A, Becherer J D. Metalloproteinase inhibitors for the disintegrin-like metalloproteinases ADAM10 and ADAM17 that differentially block constitutive and phorbol ester-inducible shedding of cell surface molecules. *Comb. Chem. High Throughput Screen* 2005; 8(2):161-71. Review.
10. Liu P C, Liu X, Li Y, Covington M, Wynn R, Huber R, Hillman M, Yang G, Ellis D, Marando C, Katiyar K, Bradley J, Abremski K, Stow M, Rupar M, Zhuo J, Li Y L, Lin Q, Burns D, Xu M, Zhang C, Qian D Q, He C, Sharief V, Weng L, Agrios C, Shi E, Metcalf B, Newton R, Friedman S, Yao W, Scherle P, Hollis G, Burn T C. Identification of ADAM10 as a Major Source of HER2 Ectodomain Sheddase Activity in HER2 Overexpressing Breast *Cancer Cells. Cancer Biol. Ther.* 200; 5(6):657-64
11. Budagian V, Bulanova E, Orinska Z, Duitman E, Brandt K, Ludwig A, Hartmann D, Lemke G, Saftig P, Bulfone-Paus S. Soluble Axl is generated by ADAM10-dependent cleavage and associates with Gas6 in mouse serum. *Mol. Cell Biol.* 2005; 25(21):9324-39.
12. Lemieux G A, Yeung N, Zhou P, Blumenkron F, Grammer A C, Lipsky P E, Moss M L and Werb Z. The low affinity IgE receptor (CD23) is cleaved by the metalloproteinase ADAM10. Submitted to *J. Biol. Chem.*
13. Postina, R., Schroeder, A., Dewachter, I., Bohl, J., Schmitt, U., Kojro, E., Prinzen, C., Endres, K., Hiemke, C., Blessing, M., Flamez, P., Dequenne, A., Godaux, E., van Leuven, F., and Fahrenholz, F. *J. Clin. Invest.* 2004; 113 (10), 1456-1464)
14. Black, R. A., Doedens, J. R., Mahimkar, R., Johnson, R., Guo, L., Wallace, A., Virca, D., Eisenman, J., Slack, J., Castner, B., Sunnarborg, S. W., Lee, D. C., Cowling, R., Jin, G., Charrier, K., Peschon, J. J., and Paxton, R. (2003)

Biochem. Soc. Symp. (70), 39-52; Sahin, U., Weskamp, G., Kelly, K., Zhou, H. M., Higashiyama, S., Peschon, J., Hartmann, D., Saftig, P., and Blobel, C. P. J. Cell. Biol. 2004; 164(5), 769-779).

15. Hart S, Fischer O M, Prenzel N, Zwick-Wallasch E, Schneider M, Hennighausen L, Ullrich A. GPCR-induced migration of breast carcinoma cells depends on both EGFR signal transactivation and EGFR-independent pathways. Biol. Chem. 2005; 386(9):845-55.

16. Rosenwasser U, Meng J. Anti-CD23. Clin. Rev. Allergy Immunol. 2005; 29(1):61-72. Review.

17. Kilmon M A, Mayer R J, Marshall L A, Conrad D H. Metalloprotease inhibitor-mediated inhibition of mouse immunoglobulin production. Immunology. 2001; 102(3): 281-8.

18. Moss M L, Bartsch J W. Therapeutic benefits from targeting of ADAM family members. Biochemistry 2004; 43(23):7227-35. Review.

19. Gonzales P E, Solomon A, Miller A B, Leesnitzer M A, Sagi I, Milla M E. Inhibition of the tumor necrosis factor-alpha-converting enzyme by its pro domain. J. Biol. Chem. 2004; 279(30):31638-45.

20. Kyte, J. and R. F. Doolittle. A simple method for displaying the hydropathic character of a protein J. Mol. Biol. 1982; 157(1):105-32.

21. Kassouf W, Luongo T, Brown G, Adam L, Dinney C P. Schedule dependent efficacy of gefitinib and docetaxel for bladder cancer J. Urol. 2006; 176(2):787-92.

22. Naus, S., Reipschlager, S., Wildeboer, D., Lichtenthaler, S. F., Mitterreiter, S., Guan, Z., Moss, M. L., and Bartsch, J. W. (2006) Biol. Chem. 387(3), 337-346.

23. Sanderson, M. P., Erickson, S, N., Gough, P. J., Garton, K. J., Wille, P. T., Raines, E. W., Dunbar, A. J., and Dempsey, P. J. (2005) J. Biol. Chem. 280(3), 1826-1837.

It will be understood that various details of the presently disclosed subject matter can be changed without departing from the scope of the presently disclosed subject matter. Furthermore, the foregoing description is for the purpose of illustration only, and not for the purpose of limitation.

---

That which is claimed is:

1. A method for inhibiting ADAM 10 activity in vitro comprising contacting a solution or a cell comprising an ADAM 10 polypeptide with an isolated ADAM 10 modulating prodomain peptide in an amount sufficient to inhibit a proteolytic activity of the ADAM 10 polypeptide, wherein the isolated ADAM 10 modulating prodomain peptide is selected from the group consisting of:
   (a) a peptide comprising an amino acid sequence at least 95% identical to SEQ ID NO: 1 beginning at amino acid 1 of SEQ ID NO: 1;
   (b) a peptide comprising an amino acid sequence at least 95% identical to SEQ ID NO: 2 beginning at amino acid 1 of SEQ ID NO: 2;
   (c) a peptide comprising an amino acid sequence at least 95% identical to SEQ ID NO: 3 beginning at amino acid 1 of SEQ ID NO: 3;
   (d) a peptide comprising an amino acid sequence at least 95% identical to SEQ ID NO: 4 beginning at amino acid 1 of SEQ ID NO: 4;
   (e) a peptide comprising an amino acid sequence at least 95% identical to SEQ ID NO: 5 beginning at amino acid 1 of SEQ ID NO: 5;
   (f) a peptide comprising an amino acid sequence at least 95% identical to SEQ ID NO: 6 beginning at amino acid 1 of SEQ ID NO: 6;
   (g) a peptide comprising an amino acid sequence at least 95% identical to SEQ ID NO: 7 beginning at amino acid 1 of SEQ ID NO: 7;
   (h) a peptide comprising an amino acid sequence at least 95% identical to SEQ ID NO: 8 beginning at amino acid 1 of SEQ ID NO: 8;
   (i) a peptide consisting of an amino acid sequence at least 95% identical to any one of SEQ ID NOs: 1-8; and
   (j) a peptide consisting of an amino acid sequence as set forth in any one of SEQ ID NOs: 1-8.

2. The method of claim 1, wherein the isolated ADAM 10 modulating prodomain peptide is a human or a mouse ADAM 10 modulating prodomain peptide.

3. The method of claim 2, wherein:
   (a) the amino acid at position 151 of SEQ ID NO: 1 is an alanine or a serine in the isolated ADAM 10 modulating prodomain peptide of 1(a);
   (b) the amino acid at position 151 of SEQ ID NO: 2 is an alanine or a serine in the isolated ADAM 10 modulating prodomain peptide of 1(b);
   (c) the amino acid at position 151 of SEQ ID NO: 3 is an alanine or a serine in the isolated ADAM 10 modulating prodomain peptide of 1(c);
   (d) the amino acid at position 156 of SEQ ID NO: 4 is an alanine or a serine in the isolated ADAM 10 modulating prodomain peptide of 1(d);
   (e) the amino acid at position 151 of SEQ ID NO: 5 is an alanine or a serine in the isolated ADAM 10 modulating prodomain peptide of 1(e);
   (f) the amino acid at position 151 of SEQ ID NO: 6 is an alanine or a serine in the isolated ADAM 10 modulating prodomain peptide of 1(f);
   (g) the amino acid at position 151 of SEQ ID NO: 7 is an alanine or a serine in the isolated ADAM 10 modulating prodomain peptide of 1(g);
   (h) the amino acid at position 156 of SEQ ID NO: 8 is an alanine or a serine in the isolated ADAM 10 modulating prodomain peptide of 1(h);
   (i) the amino acid at position 151 of any of SEQ ID NOs: 1-3 and 5-7 or the amino acid at position 156 of either of SEQ ID NOs: 4 and 8 is an alanine or a serine in the isolated ADAM 10 modulating prodomain peptide of 1(i); or
   (j) the amino acid at position 151 of any of SEQ ID NOs: 1-3 and 5-7 or the amino acid at position 156 of either of SEQ ID NOs: 4 and 8 is an alanine or a serine in the isolated ADAM 10 modulating prodomain peptide of 1(j).

4. The method of claim 1, wherein the cell comprising the ADAM 10 polypeptide is a cell growing in culture.

5. The method of claim 4, wherein the method further comprises adding the isolated ADAM 10 modulating prodomain peptide in an amount sufficient to inhibit a proteolytic activity of the ADAM 10 polypeptide to culture medium in which the cell is growing.

* * * * *

SEQUENCE LISTING

```
<160> NUMBER OF SEQ ID NOS: 20

<210> SEQ ID NO 1
<211> LENGTH: 191
<212> TYPE: PRT
<213> ORGANISM: Mus musculus
<220> FEATURE:
<221> NAME/KEY: MISC_FEATURE
<222> LOCATION: (151)..(151)
<223> OTHER INFORMATION: The Xaa at position 151 can be Cys, Ala, or Ser

<400> SEQUENCE: 1

Asn Pro Leu Asn Lys Tyr Ile Arg His Tyr Glu Gly Leu Ser Tyr Asn
1               5                   10                  15

Val Asp Ser Leu His Gln Lys His Gln Arg Ala Lys Arg Ala Val Ser
            20                  25                  30

His Glu Asp Gln Phe Leu Leu Leu Asp Phe His Ala His Gly Arg Gln
        35                  40                  45

Phe Asn Leu Arg Met Lys Arg Asp Thr Ser Leu Phe Ser Asp Glu Phe
    50                  55                  60

Lys Val Glu Thr Ser Asn Lys Val Pro Asp Tyr Asp Thr Ser His Ile
65                  70                  75                  80

Tyr Thr Gly His Ile Tyr Gly Glu Glu Gly Ser Phe Ser His Gly Ser
                85                  90                  95

Val Ile Asp Gly Arg Phe Glu Gly Phe Ile Lys Thr Arg Gly Gly Thr
            100                 105                 110

Phe Tyr Ile Glu Pro Ala Glu Arg Tyr Ile Lys Asp Arg Ile Leu Pro
        115                 120                 125

Phe His Ser Val Ile Tyr His Glu Asp Asp Ile Asn Tyr Pro His Lys
    130                 135                 140

Tyr Gly Pro Gln Gly Gly Xaa Ala Asp His Ser Val Phe Glu Arg Met
145                 150                 155                 160

Arg Lys Tyr Gln Met Thr Gly Val Glu Glu Gly Ala Arg Ala His Pro
                165                 170                 175

Glu Lys His Ala Ala Ser Ser Gly Pro Glu Leu Leu Arg Lys Lys
            180                 185                 190

<210> SEQ ID NO 2
```

```
<211> LENGTH: 159
<212> TYPE: PRT
<213> ORGANISM: Mus musculus
<220> FEATURE:
<221> NAME/KEY: MISC_FEATURE
<222> LOCATION: (151)..(151)
<223> OTHER INFORMATION: The Xaa at position 151 can be Cys, Ala, or Ser

<400> SEQUENCE: 2

Asn Pro Leu Asn Lys Tyr Ile Arg His Tyr Glu Gly Leu Ser Tyr Asn
1               5                   10                  15

Val Asp Ser Leu His Gln Lys His Gln Arg Ala Lys Arg Ala Val Ser
            20                  25                  30

His Glu Asp Gln Phe Leu Leu Leu Asp Phe His Ala His Gly Arg Gln
        35                  40                  45

Phe Asn Leu Arg Met Lys Arg Asp Thr Ser Leu Phe Ser Asp Glu Phe
    50                  55                  60

Lys Val Glu Thr Ser Asn Lys Val Pro Asp Tyr Asp Thr Ser His Ile
65                  70                  75                  80

Tyr Thr Gly His Ile Tyr Gly Glu Gly Ser Phe Ser His Gly Ser
                85                  90                  95

Val Ile Asp Gly Arg Phe Glu Gly Phe Ile Lys Thr Arg Gly Gly Thr
            100                 105                 110

Phe Tyr Ile Glu Pro Ala Glu Arg Tyr Ile Lys Asp Arg Ile Leu Pro
        115                 120                 125

Phe His Ser Val Ile Tyr His Glu Asp Asp Ile Asn Tyr Pro His Lys
    130                 135                 140

Tyr Gly Pro Gln Gly Gly Xaa Ala Asp His Ser Val Phe Glu Arg
145                 150                 155

<210> SEQ ID NO 3
<211> LENGTH: 154
<212> TYPE: PRT
<213> ORGANISM: Mus musculus
<220> FEATURE:
<221> NAME/KEY: MISC_FEATURE
<222> LOCATION: (151)..(151)
<223> OTHER INFORMATION: The Xaa at position 151 can be Cys, Ala, or Ser

<400> SEQUENCE: 3

Asn Pro Leu Asn Lys Tyr Ile Arg His Tyr Glu Gly Leu Ser Tyr Asn
1               5                   10                  15

Val Asp Ser Leu His Gln Lys His Gln Arg Ala Lys Arg Ala Val Ser
            20                  25                  30

His Glu Asp Gln Phe Leu Leu Leu Asp Phe His Ala His Gly Arg Gln
        35                  40                  45

Phe Asn Leu Arg Met Lys Arg Asp Thr Ser Leu Phe Ser Asp Glu Phe
    50                  55                  60

Lys Val Glu Thr Ser Asn Lys Val Pro Asp Tyr Asp Thr Ser His Ile
65                  70                  75                  80

Tyr Thr Gly His Ile Tyr Gly Glu Gly Ser Phe Ser His Gly Ser
                85                  90                  95

Val Ile Asp Gly Arg Phe Glu Gly Phe Ile Lys Thr Arg Gly Gly Thr
            100                 105                 110

Phe Tyr Ile Glu Pro Ala Glu Arg Tyr Ile Lys Asp Arg Ile Leu Pro
        115                 120                 125

Phe His Ser Val Ile Tyr His Glu Asp Asp Ile Asn Tyr Pro His Lys
    130                 135                 140

Tyr Gly Pro Gln Gly Gly Xaa Ala Asp His
```

<210> SEQ ID NO 4
<211> LENGTH: 159
<212> TYPE: PRT
<213> ORGANISM: Mus musculus
<220> FEATURE:
<221> NAME/KEY: MISC_FEATURE
<222> LOCATION: (156)..(156)
<223> OTHER INFORMATION: The Xaa at position 156 can be Cys, Ala, or Ser

<400> SEQUENCE: 4

Gly Gly Gln Tyr Gly Asn Pro Leu Asn Lys Tyr Ile Arg His Tyr Glu
1               5                   10                  15

Gly Leu Ser Tyr Asn Val Asp Ser Leu His Gln Lys His Gln Arg Ala
                20                  25                  30

Lys Arg Ala Val Ser His Glu Asp Gln Phe Leu Arg Leu Asp Phe His
            35                  40                  45

Ala His Gly Arg Gln Phe Asn Leu Arg Met Lys Arg Asp Thr Ser Leu
        50                  55                  60

Phe Ser Asp Glu Phe Lys Val Glu Thr Ser Asn Lys Val Pro Asp Tyr
65                  70                  75                  80

Asp Thr Ser His Ile Tyr Thr Gly His Ile Tyr Gly Glu Glu Gly Ser
                85                  90                  95

Phe Ser His Gly Ser Val Ile Asp Gly Arg Phe Glu Gly Phe Ile Lys
            100                 105                 110

Thr Arg Gly Gly Thr Phe Tyr Ile Glu Pro Ala Glu Arg Tyr Ile Lys
        115                 120                 125

Asp Arg Ile Leu Pro Phe His Ser Val Ile Tyr His Glu Asp Asp Ile
    130                 135                 140

Asn Tyr Pro His Lys Tyr Gly Pro Gln Gly Gly Xaa Ala Asp His
145                 150                 155

<210> SEQ ID NO 5
<211> LENGTH: 190
<212> TYPE: PRT
<213> ORGANISM: Homo sapiens
<220> FEATURE:
<221> NAME/KEY: MISC_FEATURE
<222> LOCATION: (151)..(151)
<223> OTHER INFORMATION: The Xaa at position 151 can be Cys, Ala, or Ser

<400> SEQUENCE: 5

Asn Pro Leu Asn Lys Tyr Ile Arg His Tyr Glu Gly Leu Ser Tyr Asn
1               5                   10                  15

Val Asp Ser Leu His Gln Lys His Gln Arg Ala Lys Arg Ala Val Ser
                20                  25                  30

His Glu Asp Gln Phe Leu Arg Leu Asp Phe His Ala His Gly Arg His
            35                  40                  45

Phe Asn Leu Arg Met Lys Arg Asp Thr Ser Leu Phe Ser Asp Glu Phe
        50                  55                  60

Lys Val Glu Thr Ser Asn Lys Val Leu Asp Tyr Asp Thr Ser His Ile
65                  70                  75                  80

Tyr Thr Gly His Ile Tyr Gly Glu Glu Gly Ser Phe Ser His Gly Ser
                85                  90                  95

Val Ile Asp Gly Arg Phe Glu Gly Phe Ile Gln Thr Arg Gly Gly Thr
            100                 105                 110

Phe Tyr Val Glu Pro Ala Glu Arg Tyr Ile Lys Asp Arg Thr Leu Pro
        115                 120                 125

```
Phe His Ser Val Ile Tyr His Glu Asp Asp Ile Asn Tyr Pro His Lys
    130                 135                 140

Tyr Gly Pro Gln Gly Gly Xaa Ala Asp His Ser Val Phe Glu Arg Met
145                 150                 155                 160

Arg Lys Tyr Gln Met Thr Gly Val Glu Val Thr Gln Ile Pro Gln
                165                 170                 175

Glu Glu His Ala Ala Asn Gly Pro Glu Leu Leu Arg Lys Lys
            180                 185                 190

<210> SEQ ID NO 6
<211> LENGTH: 159
<212> TYPE: PRT
<213> ORGANISM: Homo sapiens
<220> FEATURE:
<221> NAME/KEY: MISC_FEATURE
<222> LOCATION: (151)..(151)
<223> OTHER INFORMATION: The Xaa at position 151 can be Cys, Ala, or Ser

<400> SEQUENCE: 6

Asn Pro Leu Asn Lys Tyr Ile Arg His Tyr Glu Gly Leu Ser Tyr Asn
1               5                   10                  15

Val Asp Ser Leu His Gln Lys Gln Arg Ala Lys Arg Ala Val Ser
            20                  25                  30

His Glu Asp Gln Phe Leu Arg Leu Asp Phe His Ala His Gly Arg His
        35                  40                  45

Phe Asn Leu Arg Met Lys Arg Asp Thr Ser Leu Phe Ser Asp Glu Phe
    50                  55                  60

Lys Val Glu Thr Ser Asn Lys Val Leu Asp Tyr Asp Ser His Ile
65                  70                  75                  80

Tyr Thr Gly His Ile Tyr Gly Glu Glu Gly Ser Phe Ser His Gly Ser
                85                  90                  95

Val Ile Asp Gly Arg Phe Glu Gly Phe Ile Gln Thr Arg Gly Gly Thr
            100                 105                 110

Phe Tyr Val Glu Pro Ala Glu Arg Tyr Ile Lys Asp Arg Thr Leu Pro
        115                 120                 125

Phe His Ser Val Ile Tyr His Glu Asp Asp Ile Asn Tyr Pro His Lys
    130                 135                 140

Tyr Gly Pro Gln Gly Gly Xaa Ala Asp His Ser Val Phe Glu Arg
145                 150                 155

<210> SEQ ID NO 7
<211> LENGTH: 154
<212> TYPE: PRT
<213> ORGANISM: Homo sapiens
<220> FEATURE:
<221> NAME/KEY: MISC_FEATURE
<222> LOCATION: (151)..(151)
<223> OTHER INFORMATION: The Xaa at position 151 can be Cys, Ala, or Ser

<400> SEQUENCE: 7

Asn Pro Leu Asn Lys Tyr Ile Arg His Tyr Glu Gly Leu Ser Tyr Asn
1               5                   10                  15

Val Asp Ser Leu His Gln Lys Gln Arg Ala Lys Arg Ala Val Ser
            20                  25                  30

His Glu Asp Gln Phe Leu Arg Leu Asp Phe His Ala His Gly Arg His
        35                  40                  45

Phe Asn Leu Arg Met Lys Arg Asp Thr Ser Leu Phe Ser Asp Glu Phe
    50                  55                  60

Lys Val Glu Thr Ser Asn Lys Val Leu Asp Tyr Asp Ser His Ile
65                  70                  75                  80
```

Tyr Thr Gly His Ile Tyr Gly Glu Gly Ser Phe Ser His Gly Ser
                85                  90                  95

Val Ile Asp Gly Arg Phe Glu Gly Phe Ile Gln Thr Arg Gly Gly Thr
                100                 105                 110

Phe Tyr Val Glu Pro Ala Glu Arg Tyr Ile Lys Asp Arg Thr Leu Pro
            115                 120                 125

Phe His Ser Val Ile Tyr His Glu Asp Asp Ile Asn Tyr Pro His Lys
        130                 135                 140

Tyr Gly Pro Gln Gly Gly Xaa Ala Asp His
145                 150

<210> SEQ ID NO 8
<211> LENGTH: 159
<212> TYPE: PRT
<213> ORGANISM: Homo sapiens
<220> FEATURE:
<221> NAME/KEY: MISC_FEATURE
<222> LOCATION: (156)..(156)
<223> OTHER INFORMATION: The Xaa at position 156 can be Cys, Ala, or Ser

<400> SEQUENCE: 8

Gly Gly Gln Tyr Gly Asn Pro Leu Asn Lys Tyr Ile Arg His Tyr Glu
1               5                   10                  15

Gly Leu Ser Tyr Asn Val Asp Ser Leu His Gln Lys His Gln Arg Ala
            20                  25                  30

Lys Arg Ala Val Ser His Glu Asp Gln Phe Leu Arg Leu Asp Phe His
        35                  40                  45

Ala His Gly Arg His Phe Asn Leu Arg Met Lys Arg Asp Thr Ser Leu
    50                  55                  60

Phe Ser Asp Glu Phe Lys Val Glu Thr Ser Asn Lys Val Leu Asp Tyr
65                  70                  75                  80

Asp Thr Ser His Ile Tyr Thr Gly His Ile Tyr Gly Glu Gly Ser
                85                  90                  95

Phe Ser His Gly Ser Val Ile Asp Gly Arg Phe Glu Gly Phe Ile Gln
            100                 105                 110

Thr Arg Gly Gly Thr Phe Tyr Val Glu Pro Ala Glu Arg Tyr Ile Lys
        115                 120                 125

Asp Arg Thr Leu Pro Phe His Ser Val Ile Tyr His Glu Asp Asp Ile
    130                 135                 140

Asn Tyr Pro His Lys Tyr Gly Pro Gln Gly Gly Xaa Ala Asp His
145                 150                 155

<210> SEQ ID NO 9
<211> LENGTH: 33
<212> TYPE: DNA
<213> ORGANISM: Mus musculus

<400> SEQUENCE: 9
ggagccggat ccaatccttt aaataaatat att                          33

<210> SEQ ID NO 10
<211> LENGTH: 36
<212> TYPE: DNA
<213> ORGANISM: Mus musculus

<400> SEQUENCE: 10
ggagccgaat tcttagcgtt ttttcctcag gagctc                       36

<210> SEQ ID NO 11

```
<211> LENGTH: 33
<212> TYPE: DNA
<213> ORGANISM: Mus musculus

<400> SEQUENCE: 11
ggagcccata tgaatccttt aaataaatat att                                    33

<210> SEQ ID NO 12
<211> LENGTH: 33
<212> TYPE: DNA
<213> ORGANISM: Mus musculus

<400> SEQUENCE: 12
ggagccggat cctttttttcc tcaggagctc agg                                   33

<210> SEQ ID NO 13
<211> LENGTH: 33
<212> TYPE: DNA
<213> ORGANISM: Mus musculus

<400> SEQUENCE: 13
ggagcccata tgaatccttt aaataaatat att                                    33

<210> SEQ ID NO 14
<211> LENGTH: 33
<212> TYPE: DNA
<213> ORGANISM: Mus musculus

<400> SEQUENCE: 14
ggagccggat cccctttcaa aaacggagtg atc                                    33

<210> SEQ ID NO 15
<211> LENGTH: 45
<212> TYPE: DNA
<213> ORGANISM: Mus musculus

<400> SEQUENCE: 15
aaatacggcc cacagggcgg ctctgcagat cactccgttt ttgaa                       45

<210> SEQ ID NO 16
<211> LENGTH: 42
<212> TYPE: DNA
<213> ORGANISM: Mus musculus

<400> SEQUENCE: 16
ttcaaaaacg gagtgatctg agaccccct ggggccgtat tt                           42

<210> SEQ ID NO 17
<211> LENGTH: 8
<212> TYPE: PRT
<213> ORGANISM: Artificial sequence
<220> FEATURE:
<223> OTHER INFORMATION: Artificially synthesized flurorescently labeled
      substrate
<220> FEATURE:
<221> NAME/KEY: MISC_FEATURE
<222> LOCATION: (1)..(1)
<223> OTHER INFORMATION: Leu is modified with a 4-(4-
      Dimethylaminophenylazo)benzoyl group
<220> FEATURE:
<221> NAME/KEY: MISC_FEATURE
<222> LOCATION: (5)..(5)
<223> OTHER INFORMATION: Phe is L-Homophenylalanine (L-a-Amino-g-
      phenylbutyric acid)
<220> FEATURE:
<221> NAME/KEY: MISC_FEATURE
<222> LOCATION: (8)..(8)
<223> OTHER INFORMATION: Cys is modified with a fluorescein group
```

```
<400> SEQUENCE: 17

Leu Ala Gln Ala Phe Arg Ser Cys
1               5

<210> SEQ ID NO 18
<211> LENGTH: 8
<212> TYPE: PRT
<213> ORGANISM: Artificial sequence
<220> FEATURE:
<223> OTHER INFORMATION: Artificially synthesized fluorescently labeled
      substrate
<220> FEATURE:
<221> NAME/KEY: MISC_FEATURE
<222> LOCATION: (1)..(1)
<223> OTHER INFORMATION: Gly is modified with a 4-(4-
      Dimethylaminophenylazo)benzoyl) group
<220> FEATURE:
<221> NAME/KEY: MISC_FEATURE
<222> LOCATION: (8)..(8)
<223> OTHER INFORMATION: Cys is modified with a fluorescein group

<400> SEQUENCE: 18

Gly Pro Leu Gly Met Arg Gly Cys
1               5

<210> SEQ ID NO 19
<211> LENGTH: 6
<212> TYPE: PRT
<213> ORGANISM: Artificial sequence
<220> FEATURE:
<223> OTHER INFORMATION: Artificially synthesized fluorescently labeled
      substrate
<220> FEATURE:
<221> NAME/KEY: MISC_FEATURE
<222> LOCATION: (1)..(1)
<223> OTHER INFORMATION: Amino terminal residue is modified with a 4-(4-
      Dimethylaminophenylazo)benzoyl) group
<220> FEATURE:
<221> NAME/KEY: MISC_FEATURE
<222> LOCATION: (1)..(1)
<223> OTHER INFORMATION: The Xaa at position 1 is is proline or beta-
      cyclohexyl-L-alanine
<220> FEATURE:
<221> NAME/KEY: MOD_RES
<222> LOCATION: (3)..(3)
<223> OTHER INFORMATION: Cys3 is methylated

<400> SEQUENCE: 19

Xaa Gly Cys His Ala Lys
1               5

<210> SEQ ID NO 20
<211> LENGTH: 14
<212> TYPE: PRT
<213> ORGANISM: Artificial sequence
<220> FEATURE:
<223> OTHER INFORMATION: Artificially synthesized fluorescently labeled
      substrate
<220> FEATURE:
<221> NAME/KEY: MISC_FEATURE
<222> LOCATION: (1)..(1)
<223> OTHER INFORMATION: Position 1 is modified with a 2,4-Dinitrophenyl
      group
<220> FEATURE:
<221> NAME/KEY: MISC_FEATURE
<222> LOCATION: (2)..(2)
<223> OTHER INFORMATION: Position 2 is norleucine
<220> FEATURE:
<221> NAME/KEY: MISC_FEATURE
<222> LOCATION: (14)..(14)
<223> OTHER INFORMATION: Position 14 has a free amino group

<400> SEQUENCE: 20
```

-continued

```
Ile Leu Gln Lys Leu Asp Lys Ser Phe Ser Met Ile Lys Glu
1               5                   10
```